United States Patent [19]

Brookes et al.

[11] 4,087,269

[45] May 2, 1978

[54] HERBICIDAL TRIAZOLE CARBOXAMIDES

[75] Inventors: Robert Frederick Brookes, Tollerton; David Henry Godson, Chilwell; Douglas Greenwood; Margaret Tulley, both of Nottingham; Stanley Brice Wakerley, Burton Joyce, all of England

[73] Assignee: The Boots Company Limited, Nottingham, United Kingdom

[21] Appl. No.: 603,572

[22] Filed: Aug. 11, 1975

Related U.S. Application Data

[60] Division of Ser. No. 317,453, Dec. 21, 1972, Pat. No. 3,952,001, which is a continuation-in-part of Ser. No. 261,206, Jun. 9, 1972, abandoned, which is a continuation-in-part of Ser. No. 153,446, Jun. 15, 1971, abandoned.

[30] Foreign Application Priority Data

Jul. 1, 1970 United Kingdom ............... 31922/70
Mar. 31, 1971 United Kingdom ................ 8275/71
Dec. 31, 1971 United Kingdom ............... 61022/71
Dec. 31, 1971 United Kingdom ............... 61023/71

[51] Int. Cl.$^2$ .......................... A01N 9/12; A01N 9/14; A01N 9/16
[52] U.S. Cl. ........................................................ 71/92
[58] Field of Search ........................ 260/308 R; 71/92

[56] References Cited

U.S. PATENT DOCUMENTS 3,308,131   3/1967   McKusick ........................ 260/308 R

*Primary Examiner*—Alton D. Rollins
*Attorney, Agent, or Firm*—Lawrence Rosen; E. Janet Berry

[57] ABSTRACT

Novel 1-carbamoyl-1,2,4-triazoles, processes for their production, and herbicidal compositions and methods are described. The compounds are particularly useful for the pre-weed emergence control of the graminaceous weeds crabgrass, barnyard grass, yellow foxtail and Johnson grass.

11 Claims, No Drawings

HERBICIDAL TRIAZOLE CARBOXAMIDES

This application is a division of application Ser. No. 317,453 filed Dec. 21, 1972, now U.S. Pat. No. 3,952,001, which is a continuation-in-part of copending application Ser. No. 261,206, filed 9th June 1972, now abandoned, which is in turn a continuation-in-part of application Ser. No. 153,446, filed 15th June 1971, now abandoned.

The invention relates to new chemical compounds with herbicidal activity. More particularly, this invention relates to new 1,2,4-triazoles, herbicidal compositions containing these compounds as active ingredients, and the use of these compounds to control weeds.

In U.S. Pat. Specification No. 3,308,131 there is described a broad group of 1,2,4-triazoles of the isomeric general formulae

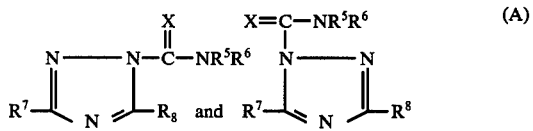

wherein X is oxygen or sulphur, $R^5$ and $R^6$ are aliphatic groups which together contain up to 14 carbon atoms and which may be joined to form a heterocyclic ring with the carbamoyl nitrogen atom, and $R^7$ and $R^8$, which together contain up to 14 carbon atoms, are free from aliphatic unsaturation and are selected from hydrogen, halogen, sulphonyl, mercapto, cyano, hydrocarbyl, halohydrocarbyl, nitrohydrocarbyl, hydrocarbyloxycarbonylhydrocarbyl, hydrocarbylsulphonyl, hydrocarbylmercapto, nitrohydrocarbylmercapto, halohydrocarbylmercapto, aminohydrocarbylmercapto and hydrocarbyloxyhydrocarbyl. The compounds in this group are stated to be effective insecticides, particularly against mites and aphids. In addition, some of the compounds are stated to have analgesic properties.

We have now found that advantageous and valuable herbicidal properties are possessed by a relatively narrow group of new 1,2,4-triazoles, some of which compounds are encompassed by the broad group of 1,2,4-triazoles defined above.

The new 1,2,4-triazoles provided by the present invention are 1-N,N-disubstituted-carbamoyl-1,2,4-triazoles with a sulphur function in the 3-position, selected from the group consisting of (a) a compound of the formula

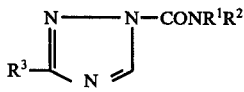

in which $R^3$ is alkylthio containing 2-5 carbon atoms, alkylsulphinyl containing 3-5 carbon atoms, alkylsulphonyl containing 1-5 carbon atoms or alkenylthio containing 3 or 4 carbon atoms, $R^1$ is alkyl containing 2-6 carbon atoms, allyl or 2-methylallyl, and $R^2$ is alkyl containing 2 or 3 carbon atoms, allyl, 2-methylallyl or prop-2-ynyl, the total number of carbon atoms in $R^1$ and $R^2$ together being 4-9 inclusive;

(b) a compound of the formula

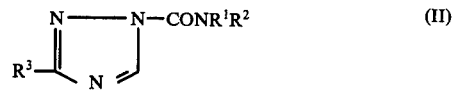

in which $R^3$ is alkylsulphonyl containing 1-5 carbon atoms, alkenyloxyalkylthio containing 4-6 carbon atoms, alkoxyalkylsulphinyl containing 2-6 carbon atoms, alkoxyalkylsulphonyl containing 2-6 carbon atoms, haloalkylsulphinyl containing 2-5 carbon atoms or haloalkylsulphonyl containing 1-5 carbon atoms, $R^1$ is alkyl containing 2-6 carbon atoms, allyl, 2-methylallyl, alkoxyalkyl containing 2-6 carbon atoms, alkenyloxyalkyl containing 4-6 carbon atoms, haloalkyl containing 2-6 carbon atoms, 2-haloallyl or 2,3-dihaloallyl, and $R^2$ is alkyl containing 2 or 3 carbon atoms, allyl, 2-methylallyl, prop-2-ynyl, alkoxyalkyl containing 2,3 or 4 carbon atoms, haloalkyl containing 2 or 3 carbon atoms, 2,3-dihaloallyl or cyclopropyl, provided that $R^2$ is cyclopropyl or that at least one of the groups $R^1$, $R^2$ and $R^3$ contains an alkoxy substituent or one or two halo substituents; and (c) a compound of the formula

in which $R^1$ is alkyl containing 1 or 2 carbon atoms, allyl, 2-methylallyl, prop-2-ynyl, alkoxyalkyl containing 2-4 carbon atoms, haloalkyl containing 1-4 carbon atoms, 2-haloallyl, 2,3-dihaloallyl or cyclopropyl, $R^2$ is alkyl containing 2-8 carbon atoms, alkenyl containing 2-8 carbon atoms, alkenyloxyalkyl containing 4-8 carbon atoms (for example allyloxyalkyl or (2-methylallyl)oxyalkyl), haloalkyl containing 2-8 carbon atoms, 2-haloallyl, 2,3-dihaloallyl, cyclopropyl or cyclohexyl, $R^3$ is alkyl containing 1-4 carbon atoms, allyl, 2-methylally, prop-2-ynyl, alkoxyalkyl containing 2-4 carbon atoms, haloalkyl containing 1-4 carbon atoms, 2-haloallyl, 2,3-dihaloallyl, cyclopropyl or phenyl containing 1-3 halo substituents, $R^4$ is alkyl containing 1-8 carbon atoms, alkenyl containing 2-8 carbon atoms, alkoxyalkyl containing 2-8 carbon atoms, alkenyloxyalkyl containing 4-8 carbon atoms (for example allyloxyalkyl or (2-methylallyl)oxyalkyl), haloalkyl containing 1-8 carbon atoms, 2-haloallyl, 2,3-dihaloallyl, cyclopropyl, or cyclohexyl, or $R^3$ and $R^4$, together with the nitrogen atom to which they are attached, form a heterocyclic ring, optionally containing 1-4 lower alkyl (preferably methyl) substituents, selected from morpholino, pyrrolidino, 1-piperidyl, hexamethyleneimino and heptamethyleneimino, provided that the total number of carbon atoms in $R^1$ and $R^2$ together is 3-9 inclusive, and when $R^3$ is a radical not containing a phenyl nucleus, the total number of carbon atoms in $R^3$ and $R^4$ together is 2-9 inclusive.

COMPOUNDS OF FORMULA I

According to one feature of the present invention there are provided new compounds of the general formula I, in which $R^3$ is alkylthio containing 2-5 carbon atoms, alkylsulphinyl containing 3-5 carbon atoms, alkylsulphonyl containing 1-5 carbon atoms or alkenylthio containing 3 or 4 carbon atoms, $R^1$ is alkyl containing 2-6 carbon atoms, allyl or 2-methylallyl, and $R^2$ is alkyl containing 2 or 3 carbon atoms, allyl, 2-methylallyl or prop-2-ynyl, the total number of carbon atoms in $R^1$ and $R^2$ together being 4-9 inclusive.

The alkyl or alkenyl radical in the group $R^3$ may have a straight or branched chain, and is preferably a primary or secondary radical. Typical values of $R^3$ include, for example methylsulphonyl, ethylthio, ethylsulphonyl, propylthio, propylsulphinyl, propylsulphonyl, isopropylthio, isopropylsulphiny isopropylsulphonyl, n-butylthio, n-butylsulphinyl, n-butylsulphony isobutylthio, isobutylsulphinyl, isobutylsulphonyl, sec. butylthio sec. butylsulphinyl, sec. butylsulphonyl, n-pentylthio, n-pentylsulphinyl, n-pentylsulphonyl, isopentylthio, isopentylsulphinyl, isopentylsulphonyl, allylthio, 2-methylallylthio and but-2-enylthio.

The radicals $R^1$ and $R^2$ may be straight chain or branched chain radicals, and are preferably primary or secondary radicals. Typical values of $R^1$ include, for example, ethyl, propyl, isopropyl, n-butyl, isobutyl, sec. butyl, n-pentyl, isopentyl, n-hexyl, allyl and 2-methylallyl. Typical values of $R^2$ include, for example, ethyl, propyl, isopropyl, allyl, 2-methylallyl and prop-2-ynyl.

Typical values of the carbamoyl radical —CONR$^1$R$^2$ include, for example, diethylcarbamoyl, diallylcarbamoyl, dipropylcarbamoyl, N-propyl-N-prop-2-ynylcarbamoyl, N-allyl-N-ethylcarbamoyl, N-allyl-N-propylcarbamoyl, N-allyl-N-n-butylcarbamoyl, N-allyl-N-isobutylcarbamoyl, N-allyl-N-n-pentylcarbamoyl, N-allyl-N-isopentylcarbamoyl, N-allyl-N-n-hexylcarbamoyl, N-isopropyl-N-propylcarbamoyl, di(isopropyl)carbamoyl, N-ethyl-N-propylcarbamoyl, N-ethyl-N-n-butylcarbamoyl, N-ethyl-N-n-pentylcarbamoyl, N-ethyl-N-n-hexylcarbamoyl, N-propyl-N-n-butylcarbamoyl, N-propyl-N-n-pentylcarbamoyl, N-propyl-N-n-hexylcarbamoyl, di(2-methylallyl)carbamoyl, N-propyl-N-isobutylcarbamoyl, N-propyl-N-sec. butylcarbamoyl and N-ethyl-N-isopentylcarbamoyl.

Preferred compounds of the present invention are those of the herinbefore defined general formula I in which (A) $R^3$ is alkylsulphonyl and the carbamoyl group CONR$^1$R$^2$ is diallylcarbamoyl, dialkylcarbamoyl, N-allyl-N-alkylcarbamoyl wherein the alkyl radical contains 2-6 carbon atoms, or N-alkyl-N-prop-2-ynylcarbamoyl, (B) $R^3$ is alkylsulphinyl containing 3-5 carbon atoms and the carbamoyl group CONR$^1$R$^2$ is diallylcarbamoyl, dipropylcarbamoyl, diethylcarbamoyl, N-allyl-N-alkylcarbamoyl wherein the alkyl radical contains 2-6 carbon atoms, or N-alkyl-N-prop-2-ynylcarbamoyl, and (C) $R^3$ is alkylthio and the carbamoyl group CONR$^1$R$^2$ is diallylcarbamoyl, N-allyl-N-alkylcarbamoyl wherein the alkyl radical contains 2-6 carbon atoms, or N-alkyl-N-prop-2-ynylcarbamoyl.

The present invention also provides herbicidal compositions which comprise as an active ingredient a compound of the hereinbefore defined formula I in association with a diluent or carrier. The diluent or carrier may be a solid or liquid, optionally in association with a surface-active agent, for example a dispersing agent, emulsifying agent or wetting agent.

According to a further feature of the invention there is provided a method for the pre-weed emergence control of graminaceous weeds which comprises applying to the locus of the weeds, for example the soil, a compound of the formula I. In particular embodiment of this feature is a method for the selective pre-weed emergence control of graminaceous weeds such as barnyard grass, crabgrass, yellow foxtail and Johnson grass is a crop area which comprises applying to the crop area a compound of the formula I at an application rate sufficient to control the weeds but substantially non-phytotoxic to the crop. The compounds of the formulae II and III, compositions thereof, and their use and preparation are further described in U.S. Pat. No. 3,952,001.

We have found that the triazole compounds of formulae I, II and III have valuable herbicidal properties against graminaceous weeds. For example, the compounds possess a high level of pre-weed emergence herbicidal activity against the graminaceous weeds crabgrass (*Digitaria sanguinalis*), barnyard grass (*Echinochloa crusgalli*), yellow foxtail (*Setaria lutescens*) and Johnson grass (*Sorghum halepense*). Futhermore, detailed trials in the glasshouse have shown that the compounds give a pre-weed emergence control of each of these weeds at application rates that cause no significant phytotoxic effect on the crops cotton, soyabean, peanut and maize when the compounds are applied prior to the emergence of these crops. Accordingly the compounds of the present invention can be used for the selective pre-emergence control of all of these weeds in these crops. This is an important advantage, since crabgrass, barnyard grass, yelow foxtail and Johnson grass are all important weeds in cotton, soyabean, peanut and maize and often occur together in these crops.

We have found that the compounds of the present invention have superior herbicidal properties to a variety of closely related 1,2,4-triazoles within the hereinbefore defined broad group of compounds described in U.S. Pat. Specification No. 3,308,131, including a representative selection of the compounds specifically exemplified in that patent specification. Detailed trials in the glasshouse have demonstrated that, in contrast to the compounds of the present invention, these closely related compounds do not possess both the above-described high level of pre-weed emergence herbicidal activity and the above-described ability to control selectively all four of the weeds crabgrass, barnyard grass, yellow foxtail and Johnson grass in cotton, soyabean, peanut and maize.

The compositions of the present invention include not only compositions in a suitable form for application but also concentrated primary compositions which may be supplied to the user and which require dilution with a suitable quantity of water or other diluent before application.

Typical compositions falling within the present invention include the following:

(A) DISPERSIONS AND DISPERSIBLE PREPARATIONS

As dispersions, the compositions comprise essentially a triazole compound of the general formula I, II or III dispersed in an aqueous medium. It is convenient to supply the consumer with a primary composition which may be diluted with water to form a dispersion having the desired concentration; the primary composition may be in any one of the following forms. It may be provided as a dispersible solution which comprises a compound of the general formula I, II or III dissolved in a water-miscible solvent with the addition of a dispersing agent. Alternatively it may be provided as a dispersible powder which comprises a compound of the general formula I, II or III and a dispersing agent. A further alternative comprises a compound of the general formula I, II or III in the form of a finely ground powder in association with a dispersing agent and intimately mixed with water to give a paste or cream. This paste or cream may if desired be added to an emulsion of oil in water to give a dispersion of active ingredient in an aqueous oil emulsion.

(B) EMULSIONS AND EMULSIFIABLE PREPARATIONS

Emulsions comprise essentially a triazole compound of the general formula I, II or III dissolved in a water-immiscible solvent which is formed into an emulsion with water in the presence of an emulsifying agent. An emulsion of the desired concentration may be formed from a primary composition of the following types. A concentrated stock emulsion may be supplied comprising a compound of the general formula I, II or III in combination with an emulsifying agent, water and a water-immiscible solvent. Alternatively there may be supplied an emulsifiable concentrate comprising a solution of a compound of the general formula I, II or III in a water-immiscible solvent containing an emulsifying agent.

(C) DUSTING POWDERS

A dusting powder comprises a triazole compound of the general formula I, II or III intimately mixed and ground with a solid pulverulent diluent, for example kaolin.

(D) GRANULAR SOLIDS

These may comprise a compound of the general formula I, II or III associated with similar diluents to those which may be employed in dusting powders, but the mixture is granulated by known methods. Alternatively they may comprise the active ingredient absorbed or absorbed on a pre-formed granular diluent for example fullers earth, attapulgite and limestone grit.

In addition to the ingredients already mentioned, the compositions of the invention may also contain other substances conventionally used in the art, the function of which may be to improve the ease of handling of the compositions or to improve their utility. For example an inert diluent such as kaolin may be included in dispersible powders in order to facilitate grinding and to provide sufficient bulk for mixing with water. As a further example, the compositions intended for dilution with water prior to application may also contain a wetting agent in order to obtain rapid wetting-out of the materials and to ensure satisfactory coverage of the soil. Also when dusts are prepared, a lubricant such as magnesium stearate may be added to the mixture to promote both easier mixing of the components and to ensure that the final product has free-flowing properties.

The compositions hereinbefore described wherein the active ingredients are present in solid form, for example dusting powders and dispersible powders, should preferably contain the compound of the general formula I, II or III in the form of very fine particles; the majority of the particles, of the order of at least 95%, should be less than 50$\mu$, with about 75% of them being 5 - 20$\mu$. The adjuvants conventionally used in such compositions are generally of this particle size or smaller. The compositions can be prepared by means of conventional grinding equipment such as a hammer mill.

The concentration of compound of the general formula I, II or III in the primary compositions which may be provided for the preparation of any of the forms in which the compositions of the invention may be used may vary widely and may be, for example, 2 - 95% w/w of the composition. It will be appreciated that this concentration will be influenced by the nature of the primary composition and the physical properties of its ingredients.

The concentration of the compound of general formula I, II or III in the compositions for application to control weeds should be at least 0.001% w/w, preferably 0.05 - 10% w/w.

In addition to a compound of the general formula I, II or III, the compositions of the present invention may contain one or more additional active ingredients, for example one or more insecticides, nematocides, or additional herbicides. Such an additional herbicide may be, for example, a substituted urea, for example diuron or monuron; a triazine, for example simazine or atrazine; a substituted acetanilide, for example propachlor; a nitrophenyl ether, for example nitrofen; a carbamate, for example chlorpropham; or a thiolcarbamate, for example EPTC or tri-allate.

The invention includes a method for the pre-weed emergence control of graminaceous weeds which comprises applying to the locus of the weeds, for example the soil, a triazole compound of the formula I, II or III. This method may be used subsequent to the emergence of the crop, for example for the pre-weed emergence control of graminaceous weeds such as barnyard grass in seeded or transplanted rice, but is often used prior to the emergence of the crop, as is usually the case with the control of crabgrass, barnyard grass, yellow foxtail and Johnson grass in cotton, soyabean, peanut and maize. When the method is used prior to the emergence of the crop, it is convenient to apply the compounds of the invention to the soil in which the crop is sown at or just prior to the time of sowing. Thus, for example, the compounds of the invention may be incorporated into the top layer of soil as part of a sowing procedure.

For the control of graminaceous weeds, the compounds of the invention are generally used at an application rate of 0.05 - 50 lb./acre, preferably 0.1 - 20 lb./acre. Selective pre-weed emergence control of weeds may be achieved in many instances at an application rate within the range 0.1 - 10 lb./acre.

The selective pre-weed emergence herbicidal activity of the compounds of the present invention is demonstrated by the results obtained in detailed trials carried out in the glasshouse. In these trials, trays of soil were sown with seeds of various weeds and crops, and then immediately sprayed with aqueous suspensions of the compounds under test at logarithmically reducing application rates of test compound within the range 8 1/32 lb./acre. Seeded trays of soil receiving no chemical treatment were used as controls. The weeds used were crabgrass (CG), barnyard grass (BG), yellow foxtail (YF) and Johnson grass (JG). The crops used were cotton (CO), soyabean (SB), maize (M) and peanut (P).

In the case of the weeds, the minimum application rate was recorded at which control of the weeds was achieved, as shown by emergent seedlings that were severely and irrecoverably stunted. In the case of the crops, the minimum application rate was recorded at which a phytotoxic effect was observed on the emergent seedlings. In some cases no phytotoxic effect on a crop was observed at the maximum application rate of test compound of 8 lb./acre, and this result was recorded as ">8." The results obtained with various compounds within the general formulae I, II and III are shown in the following Tables. In these Tables, the following abbreviations are used:

Me = methyl, Et = ethyl, Pr = propyl, Bu = butyl, Pen = pentyl, Hex = hexyl, $i$ = iso and $s$ = secondary. Alkyl radicals without the designation $i$- or $s$- signify normal radicals.

Table 1

| Compound (I) | | Minimum rate (lb./acre) | | | | | | | |
|---|---|---|---|---|---|---|---|---|---|
| | | control | | | | phytotoxicity | | | |
| $R^3$ | $NR^1R^2$ | CG | BG | YF | JG | CO | SB | M | P |
| SEt | N(allyl)$_2$ | 1/8 | 1/4 | 1/4 | 1/4 | >8 | 4 | 2 | >8 |
| SPr | " | 1/8 | 1/2 | 1/4 | 1/4 | >8 | >8 | 2 | 2 |
| Si-Pr | " | 1/16 | 1/8 | 1/4 | 1/16 | >8 | >8 | 2 | 4 |
| SBu | " | 1/4 | 1/2 | 1/2 | 1/2 | 4 | >8 | >8 | >8 |
| Si-Bu | " | 1/8 | 1/4 | 1/2 | 1/4 | >8 | >8 | 4 | >8 |
| Ss-Bu | " | 1/8 | 1/2 | 1/8 | 1/8 | >8 | >8 | 2 | 4 |
| SPen | " | 1/4 | 1/4 | 1/2 | 1/2 | >8 | >8 | >8 | >8 |
| SOPr | " | 1/16 | 1/4 | 1/16 | 1/8 | >8 | >8 | 4 | >8 |
| SOi-Pr | " | 1/4 | 1/4 | 1/2 | 1/4 | 4 | >8 | 2 | >8 |
| SOBu | " | 1/32 | 1/8 | 1/8 | 1/16 | >8 | >8 | 4 | >8 |
| SOi-Bu | " | 1/8 | 1/8 | 1/4 | 1/8 | 2 | 1 | 1 | 4 |
| SOs-Bu | " | 1/8 | 1/4 | 1/8 | 1/16 | 2 | >8 | 4 | 4 |
| SOPen | " | 1/8 | 1/16 | 1/16 | 1/16 | >8 | >8 | 2 | >8 |
| SO$_2$Me | " | 1/2 | 1/2 | 1/2 | 1/8 | 2 | >8 | 2 | >8 |
| SO$_2$Et | " | 1/16 | 1/4 | 1/16 | 1/8 | >8 | >8 | >8 | 4 |
| SO$_2$Pr | " | 1/16 | 1/8 | 1/16 | 1/8 | >8 | >8 | 4 | 1 |
| SO$_2$i-Pr | " | 1/16 | 1/16 | 1/4 | 1/16 | 2 | 4 | 2 | 4 |
| SO$_2$Bu | " | 1/8 | 1/4 | 1/4 | 1/16 | >8 | >8 | >8 | >8 |
| SO$_2$i-Bu | " | 1/16 | 1/16 | 1/8 | 1/16 | 4 | 4 | 2 | 4 |
| SO$_2$s-Bu | " | 1/16 | 1/16 | 1/8 | 1/16 | 2 | 1 | 1 | 4 |
| SO$_2$Pen | " | 1/4 | 1/4 | 1/4 | 1/16 | 4 | >8 | >8 | >8 |
| Sallyl | " | 1/4 | 1/2 | 1/4 | 1/4 | >8 | 4 | 2 | >8 |
| Sbut-2-enyl | " | 1/16 | 1 | 1/2 | 1/2 | >8 | >8 | >8 | >8 |
| SEt | N(2-Me-allyl)$_2$ | 1/4 | 1 | 1/2 | 1/4 | >8 | 4 | 4 | >8 |
| SO$_2$Et | " | 1/4 | 1/2 | 1/4 | 1/4 | 4 | >8 | 4 | >8 |
| SEt | NPr$_2$ | 1/4 | 1 | 1/4 | 1/4 | >8 | 4 | 4 | >8 |
| SPr | " | 1/4 | 1 | 1 | 1 | >8 | >8 | >8 | >8 |
| SBu | " | 1/2 | 1 | 1 | 1 | >8 | 4 | >8 | 4 |
| Si-Bu | " | 1/4 | 1 | 1 | 1 | >8 | 4 | >8 | >8 |
| Ss-Bu | " | 1/4 | 1 | 1 | 1 | >8 | >8 | >8 | >8 |
| SPen | " | 1/4 | 1/2 | 1 | 1 | >8 | >8 | >8 | >8 |
| SOPr | " | 1/4 | 1 | 1/4 | 1/4 | >8 | >8 | 4 | >8 |
| SOi-Pr | " | 1/4 | 1 | 1 | 1 | 4 | >8 | 4 | 4 |
| SOBu | " | 1/4 | 1/4 | 1/4 | 1/4 | >8 | 4 | 2 | 4 |
| SOi-Bu | " | 1/2 | 1/2 | 1/2 | 1/2 | >8 | >8 | 4 | >8 |
| SOs-Bu | " | 1/4 | 1/4 | 1/4 | 1/2 | 2 | 4 | 4 | 2 |
| SOPen | " | 1/4 | 1/8 | 1/4 | 1/16 | >8 | >8 | >8 | >8 |
| SO$_2$Me | " | 1/8 | 1/2 | 1/4 | 1/2 | 4 | 4 | 4 | >8 |
| SO$_2$Et | " | 1/32 | 1/16 | 1/8 | 1/32 | >8 | >8 | >8 | >8 |
| SO$_2$Pr | " | 1/32 | 1/32 | 1/16 | 1/16 | >8 | >8 | >8 | >8 |
| SO$_2$i-Pr | " | 1/4 | 1/4 | 1/8 | 1/4 | >8 | >8 | 4 | >8 |
| SO$_2$Bu | " | 1/32 | 1/16 | 1/16 | 1/16 | >8 | >8 | >8 | >8 |
| SO$_2$i-Bu | " | 1/16 | 1/8 | 1/8 | 1/16 | 4 | 4 | 2 | >8 |
| SO$_2$s-Bu | " | 1/16 | 1/16 | 1/16 | 1/4 | >8 | 4 | 2 | >8 |
| SO$_2$Pen | " | 1/4 | 1/4 | 1/4 | 1/4 | 4 | >8 | 4 | >8 |
| Sallyl | " | 1/2 | 1 | 1/2 | 1/4 | >8 | 4 | 4 | >8 |
| Sbut-2-enyl | " | 1/2 | 1 | 1 | 1 | >8 | >8 | >8 | >8 |
| SO$_2$Et | N(Pr)i-Pr | 1/16 | 1/8 | 1/16 | 1/8 | 2 | 2 | 1 | >8 |
| SEt | NEt$_2$ | 1/4 | 1/16 | 1/4 | 1/16 | 4 | 2 | 1 | >8 |
| SPr | " | 1/4 | 1 | 1/2 | 1/8 | >8 | >8 | 4 | >8 |
| Si-Pr | " | 1/16 | 1/4 | 1/4 | 1/16 | >8 | 2 | 1 | >8 |
| SBu | " | 1 | 1 | 1/2 | 1/2 | >8 | 4 | 2 | >8 |
| Si-Bu | " | 1/16 | 1/16 | 1/16 | 1/16 | >8 | 2 | 2 | >8 |
| Ss-Bu | " | 1/4 | 1/4 | 1/2 | 1/16 | >8 | 4 | 2 | >8 |
| SPen | " | 1/16 | 1/2 | 1/4 | 1/8 | >8 | >8 | >8 | >8 |
| SOPr | " | 1/4 | 1/4 | 1/4 | 1/4 | >8 | 4 | 2 | >8 |
| SOi-Pr | " | 1 | 1 | 1 | 1/2 | >8 | >8 | >8 | 4 |
| SOBu | " | 1/8 | 1/4 | 1/32 | 1/2 | 2 | >8 | 2 | >8 |
| SO$_2$Me | " | 1/8 | 1/8 | 1/4 | 1/8 | 4 | 1 | 2 | >8 |
| SO$_2$Et | " | 1/8 | 1/4 | 1/8 | 1/8 | 4 | 4 | 1 | 4 |
| SO$_2$Pr | " | 1/8 | 1/4 | 1/4 | 1/16 | 1 | 4 | 1 | >8 |
| SO$_2$i-Pr | " | 1/16 | 1/8 | 1/8 | 1/16 | 1 | 1 | 1 | >8 |
| SO$_2$Bu | " | 1/16 | 1/8 | 1/16 | 1/16 | 2 | 4 | 1 | 4 |
| SO$_2$i-Bu | " | 1/16 | 1/16 | 1/16 | 1/16 | 2 | 1 | 1/2 | 2 |
| SO$_2$Pen | " | 1/16 | 1/16 | 1/4 | 1/4 | 1 | 1 | 1 | 2 |
| SEt | N—Pr<br>\|<br>prop-2-ynyl | 1/16 | 1/8 | 1/8 | 1/16 | >8 | >8 | 4 | 2 |
| SO$_2$Et | " | 1/4 | 1/4 | 1/4 | 1/8 | >8 | >8 | >8 | >8 |
| Sallyl | " | 1/16 | 1/2 | 1/8 | 1/4 | 4 | 2 | 2 | >8 |
| SEt | N(allyl)Et | 1/4 | 1/4 | 1 | 1/2 | >8 | 4 | 4 | >8 |
| SEt | N(allyl)Pr | 1/4 | 1/4 | 1/4 | 1/2 | >8 | >8 | 2 | 2 |
| SEt | N(allyl)Bu | 1/4 | 1/4 | 1/4 | 1/4 | >8 | >8 | >8 | 1 |
| SEt | N(allyl)Pen | 1/8 | 1/2 | 1/4 | 1/16 | >8 | >8 | 4 | 2 |
| SEt | N(allyl)Hex | 1/4 | 1/2 | 1/2 | 1/4 | >8 | 4 | 2 | >8 |
| SEt | N(allyl)i-Bu | 1/16 | 1/2 | 1/16 | 1/8 | >8 | >8 | 2 | >8 |
| SO$_2$Et | N(allyl)Et | 1/16 | 1/16 | 1/4 | 1/16 | >8 | >8 | 2 | >8 |
| SO$_2$Et | N(allyl)Pr | 1/8 | 1/4 | 1/4 | 1/4 | 4 | 4 | 2 | >8 |
| SO$_2$Et | N(allyl)Bu | 1/4 | 1/4 | 1/4 | 1/4 | 4 | 4 | 2 | >8 |
| SO$_2$Et | N(allyl)Pen | 1/16 | 1/8 | 1/8 | 1/8 | 4 | 2 | 2 | 4 |
| SO$_2$Et | N(allyl)Hex | 1/8 | 1/8 | 1/8 | 1/8 | >8 | >8 | 1 | >8 |
| SO$_2$Et | N(allyl)i-Bu | 1/16 | 1/16 | 1/16 | 1/16 | >8 | >8 | >8 | >8 |
| SEt | N(Et)Pr | 1/2 | 1 | 1 | 1 | >8 | 4 | 2 | >8 |
| SEt | N(Et)Bu | 1/2 | 1 | 1 | 1 | >8 | 4 | 4 | >8 |

Table 1-continued

| Compound (I) | | Minimum rate (lb./acre) | | | | | | | |
|---|---|---|---|---|---|---|---|---|---|
| | | control | | | | phytotoxicity | | | |
| $R^3$ | $NR^1R^2$ | CG | BG | YF | JG | CO | SB | M | P |
| SEt | N(Et)Pen | 1/2 | 1/4 | 1 | 1 | >8 | >8 | 4 | 4 |
| SEt | N(Et)Hex | 1/2 | 1/2 | 1/2 | 1/4 | >8 | >8 | 4 | >8 |
| SEt | N(Pr)Bu | 1/2 | 1 | 1 | 1/2 | >8 | >8 | >8 | >8 |
| SEt | N(Pr)Pen | 1/4 | 1/2 | 1 | 1/4 | >8 | >8 | 4 | >8 |
| SEt | N(Et)i-Bu | 1/16 | 1 | 1/16 | 1/2 | >8 | >8 | 4 | >8 |
| SEt | N(Et)i-Pen | 1/2 | 1 | 1 | 1/16 | >8 | >8 | 4 | 4 |
| SEt | N(Pr)i-Bu | 1/2 | 1 | 1 | 1 | >8 | >8 | >8 | >8 |
| $SO_2Et$ | N(Et)Pr | 1/16 | 1/4 | 1/4 | 1/8 | >8 | 1 | 1 | >8 |
| $SO_2Et$ | N(Et)Bu | 1/8 | 1/8 | 1/4 | 1/16 | >8 | >8 | 4 | 4 |
| SOi-Bu | $NEt_2$ | 1/16 | 1/4 | 1/4 | 1/16 | 4 | 2 | 1 | >8 |
| $SO_2$s-Bu | $NEt_2$ | 1/16 | 1/16 | 1/16 | 1/16 | 2 | 1 | 1/4 | 4 |
| $SO_2$t-Bu | $NEt_2$ | 1/4 | 1/2 | 1/8 | 1/16 | >8 | >8 | >8 | >8 |
| $SO_2Et$ | $N(i-Pr)_2$ | 1/8 | 1/2 | 1 | 1 | 4 | 4 | 4 | >8 |
| $SO_2$s-Bu | $N(i-Pr)_2$ | 1/16 | 1/16 | 1/16 | 1/16 | 4 | >8 | 4 | >8 |
| $SO_2Me$ | $NBu_2$ | 1/4 | 1/2 | 1 | 1 | >8 | 4 | 4 | >8 |
| $SO_2Bu$ | $NBu_2$ | 1/4 | 1/4 | 1/4 | 1/2 | >8 | 4 | 4 | >8 |
| Sallyl | $N(allyl)_2$ | 1/4 | 1/2 | 1/4 | 1/4 | >8 | 4 | 2 | >8 |
| Sbut-2-enyl | $N(allyl)_2$ | 1/16 | 1 | 1/2 | 1/2 | >8 | >8 | >8 | >8 |
| $SO_2$t-Bu | $N(allyl)_2$ | 1/2 | 1/2 | 1/4 | 1/4 | >8 | >8 | 4 | >8 |
| $SO_2$s-Bu | $N(2-Me-allyl)_2$ | 1/8 | 1/16 | 1/8 | 1/8 | >8 | >8 | 2 | >8 |
| SEt | N(i-Bu)Et | 1/16 | 1 | 1/16 | 1/2 | >8 | >8 | 4 | >8 |
| SEt | N(s-Bu)Pr | 1/4 | 1/2 | 1/8 | 1/4 | >8 | >8 | >8 | >8 |
| $SO_2$i-Pr | N(Et)Pr | 1/32 | 1/16 | 1/32 | 1/16 | >8 | >8 | 2 | >8 |
| $SO_2Bu$ | N(Et)Pr | 1/32 | 1/32 | 1/32 | 1/32 | >8 | 4 | 1/2 | 4 |
| $SO_2$i-Bu | N(Et)Pr | 1/32 | 1/32 | 1/32 | 1/32 | 4 | 4 | 1 | 4 |
| $SO_2Pr$ | N(i-Pr)Et | 1/32 | 1/32 | 1/16 | 1/16 | 4 | 2 | 1/4 | >8 |
| $SO_2Bu$ | N(i-Pr)Et | 1/32 | 1/32 | 1/32 | 1/32 | 4 | 4 | 2 | 4 |
| $SO_2$i-Bu | N(i-Pr)Et | 1/32 | 1/32 | 1/32 | 1/32 | 2 | 2 | 1/4 | 4 |
| $SO_2Et$ | N(i-Bu)Et | 1/16 | 1/8 | 1/16 | 1/8 | >8 | >8 | 2 | >8 |
| $SO_2Pr$ | N(i-Bu)Et | 1/32 | 1/32 | 1/32 | 1/32 | 2 | 2 | 1/2 | 4 |
| $SO_2Bu$ | N(i-Bu)Et | 1/32 | 1/32 | 1/32 | 1/32 | 4 | >8 | 1/4 | >8 |
| $SO_2$t-Bu | N(Et)Bu | 1 | 1/2 | 1 | 1/4 | >8 | >8 | >8 | >8 |
| $SO_2Pr$ | N(i-Pen)Et | 1/16 | 1/16 | 1/16 | 1/16 | >8 | >8 | 1 | >8 |
| $SO_2Bu$ | N(i-Pen)Et | 1/16 | 1/16 | 1/16 | 1/16 | >8 | >8 | 4 | >8 |
| $SO_2$i-Bu | N(i-Pen)Et | 1/32 | 1/32 | 1/32 | 1/32 | >8 | 4 | 1 | >8 |
| $SO_2Pr$ | N(Hex)Et | 1/16 | 1/16 | 1/16 | 1/16 | >8 | >8 | 4 | 4 |
| $SO_2$i-Pr | N(Hex)Et | 1/16 | 1/16 | 1/8 | 1/16 | >8 | >8 | 1 | >8 |
| $SO_2Pr$ | N(i-Pr)Pr | 1/16 | 1/32 | 1/16 | 1/16 | >8 | 4 | 1 | >8 |
| $SO_2Bu$ | N(i-Pr)Pr | 1/16 | 1/32 | 1/32 | 1/32 | 4 | 4 | 1/4 | 4 |
| $SO_2$t-Bu | N(allyl)Et | 1/16 | 1/8 | 1/8 | 1/4 | >8 | >8 | >8 | >8 |
| $SO_2Pr$ | N(allyl)Et | 1/16 | 1/16 | 1/16 | 1/16 | 2 | >8 | 1/2 | >8 |
| $SO_2Pr$ | N(allyl)Pr | 1/16 | 1/16 | 1/4 | 1/4 | >8 | >8 | 1 | >8 |
| $SO_2Pr$ | N(allyl)i-Pr | 1/16 | 1/16 | 1/32 | 1/8 | 2 | 4 | 1 | 4 |
| $SO_2Pr$ | N(allyl)Bu | 1/16 | 1/16 | 1/16 | 1/16 | 4 | 4 | 2 | >8 |
| $SO_2Pr$ | N(allyl)i-Bu | 1/16 | 1/16 | 1/32 | 1/32 | 2 | 2 | 4 | 4 |
| $SO_2$i-Pr | N(allyl)Et | 1/16 | 1/16 | 1/16 | 1/16 | >8 | >8 | 4 | >8 |
| $SO_2$i-Pr | N(allyl)Pr | 1/16 | 1/16 | 1/4 | 1/4 | >8 | >8 | >8 | >8 |
| $SO_2$i-Pr | N(allyl)i-Pr | 1/16 | 1/16 | 1/16 | 1/16 | 2 | >8 | 2 | >8 |
| $SO_2Bu$ | N(allyl)Et | 1/16 | 1/16 | 1/16 | 1/16 | >8 | >8 | 1/4 | >8 |
| $SO_2Bu$ | N(allyl)Bu | 1/16 | 1/8 | 1/16 | 1/16 | >8 | >8 | >8 | >8 |
| $SO_2Bu$ | N(allyl)Hex | 1/16 | 1/2 | 1/4 | 1/4 | >8 | >8 | >8 | >8 |
| $SO_2Bu$ | N(allyl)Pr | 1/16 | 1/16 | 1/16 | 1/16 | 4 | >8 | 1 | >8 |
| $SO_2$i-Bu | N(allyl)Pr | 1/32 | 1/32 | 1/32 | 1/32 | >8 | >8 | 1 | >8 |
| $SO_2$i-Bu | N(allyl)i-Pr | 1/16 | 1/16 | 1/16 | 1/16 | 1 | 2 | 1 | >8 |
| $SO_2$i-Bu | N(allyl)Hex | 1/16 | 1/2 | 1/4 | 1/2 | >8 | >8 | 4 | >8 |
| $SO_2$s-Bu | N(allyl)Et | 1/32 | 1/32 | 1/32 | 1/32 | 4 | >8 | 1/4 | >8 |
| $SO_2$t-Bu | N(allyl)Pr | 1 | 1 | 1/2 | 1 | 4 | >8 | 4 | >8 |
| $SO_2Pr$ | N(Pr / Prop-2-ynyl) | 1 | 1/16 | 1 | 1 | >8 | >8 | >8 | >8 |
| $SO_2$i-Pr | " | 1/16 | 1/4 | 1/4 | 1/4 | >8 | >8 | 4 | 2 |
| $SO_2$s-Bu | " | 1/16 | 1/32 | 1/8 | 1/32 | 4 | >8 | >8 | >8 |
| $SO_2Et$ | N(Et)Hex | 1/16 | 1/4 | 1/2 | 1/2 | >8 | >8 | >8 | >8 |
| $SO_2Et$ | N(Et)i-Pen | 1/16 | 1/16 | 1/16 | 1/16 | 4 | 4 | 1 | >8 |
| $SO_2Et$ | N(Pr)s-Bu | 1/16 | 1/8 | 1/16 | 1/8 | >8 | >8 | >8 | >8 |
| $SO_2Et$ | N(Pr)i-Bu | 1/8 | 1/2 | 1/4 | 1/2 | 2 | >8 | 4 | >8 |
| $SO_2Et$ | N(Pr)Pen | 1/8 | 1/4 | 1/16 | 1/8 | 4 | >8 | 1 | >8 |
| $SO_2Et$ | N(Pr)Hex | 1/4 | 1/2 | 1/2 | 1/2 | >8 | >8 | 4 | >8 |

For purposes of comparison, various 1,2,4-triazoles within the scope of the isomeric formulae A but outside the scope of the formulae, I, II and III (compounds of the formula III are wholly outside the scope of formulae A), were included in the glasshouse trials described above, using application rates logarithmically reducing from 32 lb./acre. The results obtained are given in the following Tables 2 and 3, in which "*" designates a compound that is specifically exemplified in U.S. Pat. Specification No. 3,308,131. The compounds that gave no control of any of the weeds crabgrass, barnyard grass, yellow foxtail and Johnson grass at the maximum application rate of 32 lb./acre are listed in Table 3. In view of their lack of activity against the weeds, these compounds were not included in the crop tests. Of the compounds listed in Table 3, those that are believed to have been obtained as a mixture of isomers (corresponding to formulae A) containing appreciably more than 10% of each isomer, or those in which the isomeric structure is uncertain, are designated 1(2)- in the nomenclature of the carbamoyl group. The remaining compounds are believed to have been obtained substantially as the isomer given, or predominantly as this isomer with less than 10% of the other isomer.

Table 2

| Compound (I, X=0, R⁸=H) | | Minimum rate (lb./acre) | | | | | | | |
|---|---|---|---|---|---|---|---|---|---|
| | | control | | | | phytotoxicity | | | |
| R⁷ | NR⁵R⁶ | CG | BG | YF | JG | CO | SB | N | P |
| * Me | NMe₂ | 1 | 16 | 2 | 2 | 4 | 8 | 4 | 8 |
| * Cl | " | 4 | 2 | 2 | 2 | 2 | 4 | 2 | 4 |
| * Br | " | 4 | 4 | 32 | 4 | 1 | 1 | 2 | 4 |
| * SMe | " | 1 | 4 | 4 | 2 | 1 | 2 | 2 | 2 |

Table 3

Compounds with the following substituents on the 1,2,4-triazole ring gave no weed control at 32 lb./acre.

1-dimethylcarbamoyl
1-dimethylthiocarbamoyl
1(2)-dimethylthiocarbamoyl-3-ethylthio
1(2)-diethylthiocarbamoyl-3-ethylthio
1(2)-dimethylthiocarbamoyl-3-methylthio-5-methyl
1(2)-dimethylcarbamoyl-3-methylsulphonyl-5-methyl
1(2)-diethylcarbamoyl-3-methylthio-5-methyl
1(2)-N-methyl-N-n-butylcarbamoyl-3-methylthio-5-methyl
1(2)-dimethylcarbamoyl-3-ethylthio-5-methyl
1-dimethylcarbamoyl-3-dodecylthio-5-methyl
1-dimethylcarbamoyl-3-n-hexylthio
1-dimethylcarbamoyl-3-cyclohexylthio
1-dimethylcarbamoyl-3-dodecylthio
1-dimethylcarbamoyl-3-undecyl-5-methylthio
1-dimethylcarbamoyl-3-benzyl
1-dimethylcarbamoyl-3-benzylthio-5-methyl
1-dimethylcarbamoyl-3-phenyl-5-methylthio
1-dimethylcarbamoyl-3-p-nitrophenylthio-5-methyl
1-dimethylcarbamoyl-3-(2,4-dinitrophenylthio)
1-dimethylcarbamoyl-3,5-dimethyl
1-dimethylcarbamoyl-3-(2-diethylaminoethylthio)-5-methyl

Table 3 (continued)

substituents on 1,2,4-triazole ring 1-dimethylcarbamoyl-3-ethoxycarbonylmethylthio-5-methyl
1-dimethylcarbamoyl-3-(1-dimethylcarbamoyl-1,2,4-triazol-3-yldithio)
1-(4-methylpiperidinocarbonyl)
1(2)-pyrrolidinocarbonyl-3-methylthio-5-methyl
1-piperidinocarbonyl-3-ethylthio
1(2)-(4-methylpiperazinocarbonyl)-3-ethylthio
1-(1,2,3,4-tetrahydroquinolinocarbonyl)-3-ethylthio
1(2)-(N-methyl-N-methoxycarbamoyl)-3-ethylthio
1-diallylcarbamoyl
1(2)-diallylcarbamoyl-3-ethylthio-5-methyl
1-diallylcarbamoyl-3-(2-diethylaminoethylthio)
1-diallylcarbamoyl-3-methoxycarbonylmethyl
1-di(cyanomethyl)carbamoyl-3-ethylthio The results given above show that the compounds listed in Table 1 are markedly superior to the compounds listed in Tables 2 and 3 in respect of their high level of selective pre-emergence activity against all four of the weeds crabgrass, barnyard grass, yellow foxtail and Johnson grass in the crops cotton, soyabean, maize and peanut.

It can be seen from the foregoing description that the compounds of the present invention are of value for the pre-weed emergence control of graminaceous weeds in a variety of crops, for example cotton, leguminous crops such as soyabean and peanut, and cereals such as maize. However, it will be appreciated that the individual compounds of the present invention are not all equivalent in their level of herbicidal activity and selectivity characteristics. Accordingly the optimum compound for one particular use is not necessarily the optimum compound for another particular use.

Insecticidal and miticidal tests have been carried out with a variety of compounds of the present invention. The compounds tested were found to have little or no activity against insects, for example *Plutella maculipennis, Phaedon cochlearieae*, and aphids such as *Aphis fabae* and *Megoura viciae*. The compounds tested were also found to have little or no activity against mites, for example *Tetranychus urticae*.

Regarding the mammalian toxicity of the compounds of the present invention, acute oral toxicity studies in mice have given satisfactory results. In these studies, the compounds of the present invention have been found to be less toxic than certain closely related 1,2,4-triazoles, for example 1-dimethylcarbamoyl-3-methylthio-1,2,4-triazole.

PREPARATION OF COMPOUNDS OF FORMULA I

The compounds of formula I may be prepared by the hereinafter described processes, which are analogous to known processes for preparing similar compounds.

One such process comprises reacting a triazole of the general formula

in which R³ is as hereinbefore defined for formula I, with a carbamoyl halide of the general formula Z-CONR¹R² (V) in which R¹ and R² are as hereinbefore defined for formula I and Z is chlorine, fluorine or bromine, preferably chlorine. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine, in order to absorb the hydrogen halide produced in the reaction. In an alternative procedure, the triazole of the general formula IV may be converted to an alkali metal (for example sodium) salt thereof prior to the reaction with the carbamoyl halide. The alkali metal salt may be obtained by reacting the triazole of the general formula IV with an alkali metal hydride, amide or alkoxide, in accordance with known methods.

The carbamoyl halides of the general formula V may be prepared by reacting a secondary amine of the general formula HNR¹R², in which R¹ and R² are as defined above, with a carbonyl halide COZ₂, in accordance with known methods.

The compounds of formula I may also be prepared by a process which comprises reacting a carbamoyl halide of the general formula

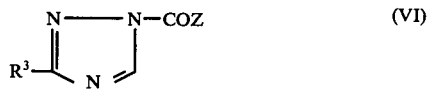

in which $R^3$ and Z are as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants. Advantageously the reaction is effected in the presence of a suitable acid-binding agent, for example a tertiary amine such as triethylamine or pyridine.

The carbamoyl halides of general formula VI may be prepared from the triazoles of general formula IV by reaction with a carbonyl halide $COZ_2$, preferably phosgene, in accordance with known methods.

The triazoles of general formula IV may be prepared by alkylation or alkenylation of 3-mercapto-1,2,4-triazole, followed by oxidation of the 3-alkylthio group where appropriate in accordance with known methods.

The compounds of formula I may also be prepared by a process which comprises reacting a carbonylbistriazole of the general formula

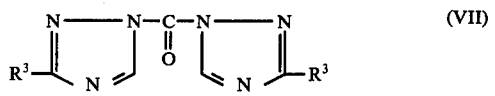
(VII)

in which $R^3$ is as defined above, with a secondary amine of the general formula $HNR^1R^2$, in which $R^1$ and $R^2$ are as defined above. The reaction is suitably effected in the presence of an inert organic liquid as the reaction medium, which is preferably a solvent for the reactants.

The carbonylbistriazoles of the general formula VII may be prepared by reacting a triazole of the hereinbefore defined general formula IV with about 0.5 molecular proportions of a carbonyl halide $COZ_2$, preferably phosgene, in accordance with known methods. The reaction is preferably effected in the presence of a suitable acid-binding agent, for example pyridine. After formation of the carbonylbistriazole, it is often convenient to react it, without isolation, with the amine of general formula $NHR^1R^2$.

It will be appreciated by those skilled in the art that the triazoles represented by the general formula IV are tautomeric and that, for convenience, general formula IV depicts the structure of one tautomer.

The compounds of formula I in which $R^3$ is an alkylsulphinyl or alkylsulphonyl group may also be prepared by a process which comprises the oxidation of a compound of the general formula

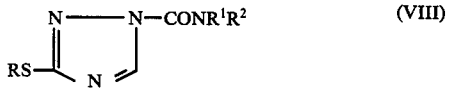
(VIII)

in which R is an appropriate alkyl group and $R^1$ and $R^2$ are as defined above, in accordance with known methods. The oxidation may be effected, for example, by reaction with hydrogen peroxide or peracetic acid.

It will be appreciated by those skilled in the art that the acylation reactions described above in the preparations of compounds of formulae I, II and III can theoretically give two isomeric products, one (hereinafter referred to as 1-isomer) having the general formula I, II or III and the other (hereinafter referred to as 2-isomer) having the general formula

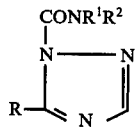

where R is the group $R^3$ of formulae I or II or the group $R^3R^4NO_2S$- of formula III.

It is believed that the solid compounds of the present invention, after purification by standard methods such as crystallization, are obtained as substantially pure 1-isomer. The liquid compounds of the present invention, as isolated by standard methods such as distillation in vacuo, are believed to be obtained as components of an isomeric mixture consisting predominantly of the 1-isomer together with a minor proportion, generally less than about 10% of 2-isomer.

The following Examples illustrate the invention.

EXAMPLE 1

Dipropylcarbamoyl chloride (5.4 g.) was added to a solution of 5.25 g. 3-propylsulphonyl-1,2,4-triazole and 6 ml. dry triethylamine in 25 ml. dry tetrahydrofuran and the resulting mixture was refluxed under anhydrous conditions for 2.5 hours. The cooled reaction mixture was filtered to remove triethylamine hydrochloride, the filtrate was distilled under reduced pressure to remove solvent, and the residue was dissolved in methylene dichloride. The resulting solution was washed with ice-cold 0.1N aqueous sodium hydroxide (2 × 50 ml.), then with 0.01N aqueous sulphuric acid (50 ml.) and finally with water. The resulting solution was dried over anhydrous sodium sulphate and was then distilled under reduced pressure to give a solid residue. This residue was recrystallized twice from petroleum ether (b.p. 60° – 80° C.) to give 1-dipropylcarbamoyl-3-propylsulphonyl-1,2,4-triazole, m.p. 79° – 80° C. Elemental analysis satisfactory.

The 3-propylsulphonyl-1,2,4-triazole used in the above reaction was prepared as follows.

3-Mercapto-1,2,4-triazole (20.2 g.) was added to a solution of 4.8 g. sodium in 150 ml. absolute ethanol. When dissolution was complete 24.6 g. propyl bromide was added. The stirred mixture was gradually heated to boiling under reflux, refluxed for 1 hour, cooled to room temperature and filtered. The filtrate was distilled to dryness under reduced pressure and the residue was dissolved in ether. The resulting solution was filtered, dried over anhydrous sodium sulphate and distilled under reduced pressure to give 3-propylthio-1,2,4-triazole, b.p. 143° – 144° C./1 mm. This product solidified, m.p. 53° – 56° C.

To a solution of 14.3 g. 3-propylthio-1,2,4-triazole in 100 ml. glacial acetic acid was added 28.5 ml. 100 vol. hydrogen peroxide solution (2.5 molecular proportions). The solution was heated gradually to 95° – 100° C., kept at this temperature for 2 hours and then distilled to dryness under reduced pressure. The residue was recrystallized from toluene to give 3-propylsulphonyl-1,2,4-triazole, m.p. 116° – 117° C. Elemental analysis satisfactory.

EXAMPLE 2

A mixture of 5.75 g. 3-propylthio-1,2,4-triazole, 6.8 g. diallylcarbamoyl chloride, 25 ml. dry tetrahydrofuran and 8 ml. dry triethylamine was refluxed under anhydrous conditions for 3 hours. The reaction mixture was worked up as described in Example 1 to produce an oil which was distilled under reduced pressure to give 1-diallylcarbamoyl-3-propylthio-1,2,4-triazole, b.p. 134° – 135° C./0.1 mm. Gas-liquid chromatographic (GLC) assay indicated a content of 1-isomer of 94.2%. Elemental analysis satisfactory.

The diallylcarbamoyl chloride used in the above preparation was prepared as follows. Phosgene was passed into refluxing ethyl acetate (100 ml.) until the liquid was saturated with phosgene. To the refluxing, stirred solution was added dropwise a solution of diallylamine (50 g.) in ethyl acetate (100 ml.), maintaining a brisk flow of phosgene. The rate of addition of the solution of diallylamine was such that solid diallylamine hydrochloride did not accumulate in the reaction mixture. When the addition was complete, the flow of phosgene into the stirred, refluxing reaction mixture was maintained for 30 minutes. The reaction mixture was distilled under reduced pressure to remove the solvent and give the product, diallylcarbamoyl chloride, as an oil, b.p. 67° – 69° C./3 mm.

EXAMPLE 3

3-n-Butylthio-1,2,4-triazole, m.p. 35° – 37° C., was prepared by alkylation of 3-mercapto-1,2,4-triazole in an analogous manner to that described in Example 1.

A mixture of 6.3 g. 3-n-butylthio-1,2,4-triazole, 6.8 g. diallylcarbamoyl chloride, 25 ml. tetrahydrofuran and 8 ml. dry triethylamine was refluxed under anhydrous conditions for 4 hours. The reaction mixture was worked up as described in Example 1 to produce an oil which was distilled under reduced pressure to give 1-diallylcarbamoyl-3-n-butylthio-1,2,4-triazole, b.p. 157° C./0.6 mm. (95.0% 1-isomer by GLC assay). Elemental analysis satisfactory.

EXAMPLE 4

3-n-Pentylthio-1,2,4-triazole, m.p. 54° – 56° C., was prepared by alkylation of 3-mercapto-1,2,4-triazole in an analogous manner to that described in Example 1.

A mixture of 9.5 g. 3-n-pentylthio-1,2,4-triazole, 8.07 g. diallylcarbamoyl chloride, 100 ml. dry tetrahydrofuran and 8 ml. dry triethylamine was refluxed under anhydrous conditions for 68 hours. The reaction mixture was worked up as described in Example 1, using ether in place of methylene dichloride, to produce an oil which was distilled under reduced pressure to give 1-diallylcarbamoyl-3-n-pentylthio-1,2,4-triazole, b.p. 135° C./0.1 mm. (90.6% 1-isomer by GLC assay). Elemental analysis satisfactory.

EXAMPLE 5

A mixture of 5.25 g. 3-propylsulphonyl-1,2,4-triazole, 5.3 g. diallylcarbamoyl chloride, 25 ml. dry tetrahydrofuran and 6 ml. dry triethylamine was refluxed under anhydrous conditions for 1.5 hours. The reaction mixture was worked up as described in Example 1 to give a solid product which was recrystallized from petroleum ether (b.p. 60° – 80° C.) to give 1-diallylcarbamoyl-3-propylsulphonyl-1,2,4-triazole, m.p. 41° – 42° C. Elemental analysis satisfactory.

EXAMPLE 6

3-Isopropylthio-1,2,4-triazole, m.p. 77° – 80° C., was prepared by alkylation of 3-mercapto-1,2,4-triazole in a manner analogous to that described in Example 1.

A mixture of 5.75 g. 3-isopropylthio-1,2,4-triazole, 6.8 g. diallylcarbamoyl chloride, 25 ml. dry tetrahydrofuran and 8 ml. dry triethylamine was refluxed under anhydrous conditions for 2.5 hours. The reaction mixture was worked up as described in Example 1 to produce an oily residue which was distilled under reduced pressure to give 1-diallylcarbamoyl-3-isopropylthio-1,2,4-triazole, b.p. 133° C./0.4 mm. – 144° C./0.9 mm. (97.2% 1-isomer by GLC assay). Elemental analysis satisfactory.

EXAMPLE 7

3-Isobutylthio-1,2,4-triazole, m.p. 61° – 63.5° C., was prepared by alkylation of 3-mercapto-1,2,4-triazole in an analogous manner to that described in Example 1.

A mixture of 7.85 g. 3-isobutylthio-1,2,4-triazole, 10.97 g. diallylcarbamoyl chloride, 100 ml. dry tetrahydrofuran and 11 ml. dry triethylamine was refluxed under anhydrous conditions for 48 hours. The reaction mixture was worked up as described in Example 1, using ether in place of methylene dichloride. An oily residue was obtained which was distilled under reduced pressure to give 1-diallylcarbamoyl-3-isobutylthio-1,2,4-triazole, b.p. 116° – 118° C./0.5 mm. (96.0% 1-isomer by GLC assay).

The following compounds were prepared in an analogous manner.

1-dipropylcarbamoyl-3-n-butylthio-1,2,4-triazole,
b.p. 140° – 141° C./0.1 mm. (92.4% 1-isomer by GLC assay).
1-dipropylcarbamoyl-3-isobutylthio-1,2,4-triazole,
b.p. 128° – 129° C./0.15 mm. (92.1% 1-isomer by GLC assay).
1-dipropylcarbamoyl-3-sec.butylthio-1,2,4-triazole,
b.p. 140° – 142° C./0.5 mm. (90.8% 1-isomer by GLC assay).
1-dipropylcarbamoyl-3-n-pentylthio-1,2,4-triazole,
b.p. 140° – 142° C./0.1 mm. (81.4% 1-isomer by GLC assay).

Satisfactory elemental analyses were obtained for all the above compounds.

EXAMPLE 8

3-Mercapto-1,2,4-triazole was alkylated to 3-methylthio-1,2,4-triazole, m.p. 103° – 104° C., and this compound was oxidized to 3-methylsulphonyl-1,2,4-triazole, m.p. 202° C., by methods analogous to those described in Example 1.

Dipropylcarbamoyl chloride (5.5 g.) was added to a solution of 4.4 g. 3-methylsulphonyl-1,2,4-triazole and 6 ml. dry triethylamine in 25 ml. dry tetrahydrofuran and the resulting mixture refluxed for 2.5 hours under anhydrous conditions. The cooled reaction mixture was filtered to remove triethylamine hydrochloride and the filtrate poured with stirring into 150 ml. ice-cold 0.1N aqueous sodium hydroxide. The precipitated product was collected by filtration, washed with ice-cold water, dried, and crystallized twice from toluene to give 1-dipropylcarbamoyl-3-methylsulphonyl-1,2,4-triazole, m.p. 94° C. Elemental analysis satisfactory.

EXAMPLE 9

3-n-Butylsulphonyl-1,2,4-triazole, m.p. 96° – 97° C., was prepared by oxidation of 3-n-butylthio-1,2,4-triazole in an analogous manner to that described in Example 1.

A mixture of 5.7 g. 3-n-butylsulphonyl-1,2,4-triazole, 5.4 g. dipropylcarbamoyl chloride, 25 ml. dry tetrahydrofuran and 6 ml. dry triethylamine was refluxed under anhydrous conditions for 1.5 hours. The reaction mixture was worked up as described in Example 1 to produce a solid product which was recrystallized from petroleum ether (60° – 80° C.) to give 1-dipropylcarbamoyl-3-n-butylsulphonyl-1,2,4-triazole, m.p. 46° – 47° C. Elemental analysis satisfactory.

In an analogous manner there was prepared 1-dipropylcarbamoyl-3-n-pentylsulphonyl-1,2,4-triazole, m.p. 38.5° – 39.5° C. (from petroleum ether, b.p. 60° – 68° C.). Elemental analysis satisfactory.

EXAMPLE 10

3-n-Pentylsulphonyl-1,2,4-triazole, m.p. 108° – 109° C., was prepared by the oxidation of 3-n-pentylthio-1,2,4-triazole in an analogous manner to that described in Example 1.

A mixture of 10.2 g. 3-pentylsulphonyl-1,2,4-triazole, 8.2 g. diallylcarbamoyl chloride, 75 ml. dry tetrahydrofuran and 7.5 ml. dry triethylamine was refluxed under anhydrous conditions for 1.5 hours. The reaction mixture was worked up as described in Example 1, using ether in place of methylene dichloride. An oily residue was obtained which was distilled under reduced pressure to give a product, b.p. 193° – 194° C./0.25 mm., which solidified on cooling. This product was recrystallized from petroleum ether (b.p. 60° – 80° C.) to give 1-diallylcarbamoyl-3-n-pentylsulphonyl-1,2,4-triazole, m.p. 28° – 30° C. Elemental analysis satisfactory.

EXAMPLE 11

A mixture of 5.7 g. 3-butylsulphonyl-1,2,4-triazole, 5.3 g. diallylcarbamoyl chloride, 25 ml. dry tetrahydrofuran and 6 ml. dry triethylamine was refluxed under anhydrous conditions for 1.5 hours. The reaction mixture was worked up as described in Example 1 to give 1-diallylcarbamoyl-3-butylsulphonyl-1,2,4-triazole as an oil which was heated under reduced pressure (100° C./0.5 mm.) for 30 minutes to remove all traces of volatile material. Refractive index of product $n_D^{26}$ 1.5132. Elemental analysis satisfactory.

EXAMPLE 12

3-Isopropylsulphonyl-1,2,4-triazole, m.p. 170° – 171° C., was prepared by the oxidation of 3-isopropylthio-1,2,4-triazole by a method analogous to that described in Example 1.

A mixture of 7.0 g. 3-isopropylsulphonyl-1,2,4-triazole, 7.0 ml. diallylcarbamoyl chloride, 25 ml. dry tetrahydrofuran and 8 ml. dry triethylamine was refluxed for 1 hour under anhydrous conditions. The reaction mixture was worked up as described in Example 1 to give 1-diallylcarbamoyl-3-isopropylsulphonyl-1,2,4-triazole as an oil which was heated under reduced pressure (100° C./0.5 mm.) for 1 hour to remove all traces of volatile material. Refractive index of product $n_D^{26}$ 1.5158. Elemental analysis satisfactory.

EXAMPLE 13

3-Ethylthio-1,2,4-triazole, m.p. 63° – 64° C., was prepared by alkylation of 3-mercapto-1,2,4-triazole in an analogous manner to that described in Example 1.

Diallylcarbamoyl chloride (8 g.) was added to a solution of 7.1 g. 3-ethylthio-1,2,4-triazole and 8 ml. dry triethylamine in 50 ml. dry tetrahydrofuran and the mixture refluxed for 4 hours under anhydrous conditions. The cooled reaction mixture was diluted with 100 ml. toluene and washed, firstly with 1N aqueous sodium hydroxide and then with water. The resulting solution was dried over anhydrous sodium sulphate and distilled under reduced pressure to remove the solvent and give 1-diallylcarbamoyl-3-ethylthio-1,2,4-triazole, b.p. 120° – 122° C./0.1 mm. (97.1% 1-isomer by GLC assay).

The following compounds were prepared in an analogous manner.

1-dipropylcarbamoyl-3-ethylthio-1,2,4-triazole, b.p. 118° – 120° C./0.05 mm. (92.1% 1-isomer by GLC assay).

1-dipropylcarbamoyl-3-propylthio-1,2,4-triazole, b.p. 136° C./0.15 mm. (92.6% 1-isomer by GLC assay).

Satisfactory elemental analyses were obtained for all of the above compounds.

EXAMPLE 14

To a solution of 15.7 g. 3-butylthio-1,2,4-triazole in 60 ml. glacial acetic acid was added 100 vol. hydrogen peroxide solution (11.4 ml., 1 molecular proportion). The reaction mixture was cooled occasionally during 1 hour to maintain the reaction temperature at 25° – 30° C., and then kept at room temperature for 24 hours. The resulting solution was distilled under reduced pressure to produce a solid residue which was recrystallized from ethyl acetate to give 3-n-butylsulphinyl-1,2,4-triazole, m.p. 82° – 83° C.

A mixture of 5.2 g. 3-butylsulphinyl-1,2,4-triazole, 6.0 g. diallylcarbamoyl chloride, 25 ml. dry tetrahydrofuran and 7.5 ml. dry triethylamine was refluxed under anhydrous conditions for 2 hours. The reaction mixture was filtered to remove triethylamine hydrochloride and the filtrate distilled under reduced pressure to remove solvent. Finally the residue was maintained at 100° C./0.5 mm. for 30 minutes in order to remove all traces of volatile material from the product. The product, 1-diallylcarbamoyl-3-n-butylsulphinyl-1,2,4-triazole, was obtained as an oil, $n_D^{26}$ 1.5277. Elemental analysis satisfactory.

In a similar manner, the following compounds were obtained as oils with satisfactory elemental analyses.

1-diallylcarbamoyl-3-propylsulphinyl-1,2,4-triazole, $n_D^{26}$ 1.5314.

1-diallylcarbamoyl-3-n-pentylsulphinyl-1,2,4-triazole, $n_D^{26}$ 1.5247.

1-diallylcarbamoyl-3-isobutylsulphinyl-1,2,4-triazole, $n_D^{25}$ 1.5272.

1-dipropylcarbamoyl-3-n-pentylsulphinyl-1,2,4-triazole, $n_D^{26}$ 1.5068.

1-dipropylcarbamoyl-3-isobutylsulphinyl-1,2,4-triazole, $n_D^{25}$ 1.5066.

1-diethylcarbamoyl-3-t.butylsulphinyl-1,2,4-triazole, m.p. 65° – 67° C.

1-diethylcarbamoyl-3-sec.butylsulphinyl-1,2,4-triazole, $n_D^{26}$ 1.5182.

The intermediate 3-alkylsulphinyl-1,2,4-triazoles used in the above reactions were prepared by oxidation of the appropriate 3-alkylthio-1,2,4-triazoles in a manner analogous to that described above for 3-n-butylsulphinyl-1,2,4-triazole. The physical characteristics of these intermediate compounds are as follows.

3-propylsulphinyl-1,2,4-triazole, m.p. 67° – 68° C.
3-n-pentylsulphinyl-1,2,4-triazole, m.p. 62° – 63° C.
3-isobutylsulphinyl-1,2,4-triazole, m.p. 89.5° – 91.5° C.
3-sec.butylsulphinyl-1,2,4-triazole, m.p. 78° – 80° C.
3-t.butylsulphinyl-1,2,4-triazole, m.p. 163° C. (with decomposition).

EXAMPLE 15

3-Ethylsulphinyl-1,2,4-triazole, m.p. 86° – 88° C., was prepared by the oxidation of 3-ethylthio-1,2,4-triazole in a manner analogous to that described in Example 14.

A mixture of 4.35 g. 3-ethylsulphinyl-1,2,4-triazole, 6.0 ml. diallylcarbamoyl chloride, 25 ml. dry tetrahydrofuran and 7.5 ml. dry triethylamine was refluxed under anhydrous conditions for 2 hours. The reaction mixture was filtered and the filtrate distilled under reduced pressure to remove solvent, giving a residual oil which solidified on cooling. This solid product was recrystallized from petroleum ether (b.p. 60° – 80° C.) to give 1-diallylcarbamoyl-3-ethylsulphinyl-1,2,4-triazole, m.p. 41° – 43° C. Elemental analysis satisfactory.

EXAMPLE 16

A mixture of 4.1 g. 3-methylsulphonyl-1,2,4-triazole, 4.75 g. diallylcarbamoyl chloride, 20 ml. dry tetrahydrofuran and 5.5 ml. dry triethylamine was refluxed under anhydrous conditions for 1 hour. The reaction mixture was filtered and the filtrate was distilled to dryness under reduced pressure. The solid residue was recrystallized from a mixture of toluene and petroleum ether (b.p. 40° – 60° C.) to give 1-diallylcarbamoyl-3-methylsulphonyl-1,2,4-triazole, m.p. 52° – 54° C. Elemental analysis satisfactory.

EXAMPLE 17

3-Ethylsulphonyl-1,2,4-triazole, m.p. 145° C., was prepared by the oxidation of 3-ethylthio-1,2,4-triazole in an analogous manner to that described in Example 1.

A mixture of 6.45 g. 3-ethylsulphonyl-1,2,4-triazole, 6.6 g. diallylcarbamoyl chloride, 25 ml. dry tetrahydrofuran and 8 ml. dry triethylamine was refluxed under anhydrous conditions for 1.5 hours. The cooled reaction mixture was filtered and the filtrate distilled under reduced pressure to remove solvent and give a product which distilled at 187° C./0.2 mm. This product solidified and was recrystallized from petroleum ether (b.p. 60° – 80° C.) to give 1-diallylcarbamoyl-3-ethylsulphonyl-1,2,4-triazole, m.p. 39° – 42° C. Elemental analysis satisfactory.

In an analogous manner there was prepared 1-(N-isopropyl-N-propylcarbamoyl)-3-ethylsulphonyl-1,2,4-triazole, b.p. 176° – 178° C./0.2 mm. (93.3% 1-isomer by GLC assay). Elemental analysis satisfactory.

EXAMPLE 18

3-Isopropylsulphinyl-1,2,4-triazole, m.p. 105° – 107° C., was prepared by the oxidation of 3-isopropylthio-1,2,4-triazole in a manner analogous to that described in Example 14. Elemental analysis satisfactory.

A mixture of 6.4 g. 3-isopropylsulphinyl-1,2,4-triazole, 8.0 ml. diallylcarbamoyl chloride, 25 ml. dry tetrahydrofuran and 10 ml. dry triethylamine was refluxed under anhydrous conditions for 2 hours. The cooled reaction mixture was filtered and the filtrate was distilled under reduced pressure to give an oily residue which subsequently solidified. This solid residue was recrystallized from petroleum ether (b.p. 60° – 80° C.) to give 1-diallylcarbamoyl-3-isopropylsulphinyl-1,2,4-triazole, m.p. 32° – 34° C. Elemental analysis satisfactory.

EXAMPLE 19

A mixture of 4.8 g. 3-propylsulphinyl-1,2,4-triazole, 6.0 ml. dipropylcarbamoyl chloride, 25 ml. dry tetrahydrofuran and 7.5 ml. dry triethylamine was refluxed under anhydrous conditions for 2 hours. The cooled reaction mixture was filtered and the filtrate distilled under reduced pressure to give an oily residue which crystallized on trituration with petroleum ether (b.p. 60° – 80° C.). The resulting solid product was recrystallized from petroleum ether (b.p. 60° – 80° C.) to give 1-dipropylcarbamoyl-3-propylsulphinyl-1,2,4-triazole, m.p. 50° – 52° C. Elemental analysis satisfactory.

EXAMPLE 20

A mixture of 6.9 g. 3-n-butylsulphinyl-1,2,4-triazole, 8.0 ml. dipropylcarbamoyl chloride, 25 ml. dry tetrahydrofuran and 10 ml. dry triethylamine was refluxed under anhydrous conditions for 2 hours. The cooled reaction mixture was filtered and the filtrate distilled under reduced pressure to give an oily residue which subsequently solidified. This solid product was recrystallized from petroleum ether to give 1-dipropylcarbamoyl-3-n-butylsulphinyl-1,2,4-triazole, m.p. 39° – 40° C. Elemental analysis satisfactory.

EXAMPLE 21

A mixture of 6.4 g. 3-isopropylsulphinyl-1,2,4-triazole, 8.0 ml. dipropylcarbamoyl chloride, 25 ml. dry tetrahydrofuran and 10 ml. dry triethylamine was refluxed under anhydrous conditions for 2 hours. The cooled reaction mixture was filtered and the filtrate distilled under reduced pressure to give 1-dipropylcarbamoyl-3-isopropylsulphinyl-1,2,4-triazole as an oily residue which subsequently solidified, m.p. 15° – 20° C. Elemental analysis satisfactory.

EXAMPLE 22

In an analogous manner to that described in Example 20, 3-ethylsulphonyl-1,2,4-triazole was reacted with dipropylcarbamoyl chloride to give 1-dipropylcarbamoyl-3-ethylsulphonyl-1,2,4-triazole, m.p. 44° – 45° C. Elemental analysis satisfactory.

EXAMPLE 23

In an analogous manner to that described in Example 20, 3-isopropylsulphonyl-1,2,4-triazole was reacted with dipropylcarbamoyl chloride (4 hours reflux) to give 1-dipropylcarbamoyl-3-isopropylsulphonyl-1,2,4-triazole, m.p. 61° – 63° C. Elemental analysis satisfactory.

EXAMPLE 24

3-Sec.butylthio-1,2,4-triazole, b.p. 107° – 109° C./0.07 mm. was prepared by the alkylation of 3-mercapto-1,2,4-triazole in an analogous manner to that described in Example 1.

A mixture of 7.9 g. 3-sec.butylthio-1,2,4-triazole, 8.0 g. diallylcarbamoyl chloride, 100 ml. dry tetrahydrofuran and 8 ml. dry triethylamine was refluxed under anhydrous conditions for 24 hours. The reaction mixture was worked up as described in Example 1, using ether in place of methylene dichloride, to produce an oil which was distilled under reduced pressure to give 1-diallylcarbamoyl-3-sec.butylthio-1,2,4-triazole, b.p. 121° – 123° C./0.1 mm. (96.0% 1-isomer by GLC assay). Elemental analysis satisfactory.

EXAMPLE 25

3-Sec.butylsulphonyl-1,2,4-triazole, m.p. 128° – 130° C., was prepared by the oxidation of 3-sec.butylthio-1,2,4-triazole in an analogous manner to that described in Example 1.

A mixture of 9.5 g. 3-sec.butylsulphonyl-1,2,4-triazole, 7.97 g. diallylcarbamoyl chloride, 50 ml. dry tetrahydrofuran and 7.5 ml. dry triethylamine was refluxed under anhydrous conditions for 5 hours. The reaction mixture was worked up by a method analogous to that described in Example 1 to give an oil which was not distilled but was heated under reduced pressure (95° C./0.1 mm.) for 4 hours to remove traces of volatile material. The resulting product, 1-diallylcarbamoyl-3-sec.butylsulphonyl-1,2,4-triazole, was obtained as an oil, $n_D^{26}$ 1.5174. (98.9% 1-isomer by GLC assay). Elemental analysis satisfactory.

EXAMPLE 26

3-Sec.butylsulphinyl-1,2,4-triazole, m.p. 78° – 80° C., was prepared by the oxidation of 3-sec.butylthio-1,2,4-triazole in a manner analogous to that described in Example 14.

A mixture of 5.76 g. 3-sec.butylsulphinyl-1,2,4-triazole, 5.31 g. diallylcarbamoyl chloride, 50 ml. dry tetrahydrofuran and 5 ml. dry triethylamine was kept under anhydrous conditions at room temperature for 72 hours. The reaction mixture was filtered and the filtrate evaporated under reduced pressure at room temperature to give a residual oil which was dissolved in methylene dichloride. The resulting solution was washed with water, dried over anhydrous sodium sulphate and distilled under reduced pressure at room temperature to give 1-diallylcarbamoyl-3-sec.butylsulphinyl-1,2,4-triazole as a residual oil, $n_D^{25}$ 1.5268, for which a satisfactory elemental analysis was obtained.

In an analogous manner, using a reaction time of 168 hours at room temperature, there was obtained 1-dipropylcarbamoyl-3-sec.butylsulphinyl-1,2,4-triazole as a residual oil, $n_D^{25}$ 1.5078. Elemental analysis satisfactory.

EXAMPLE 27

A mixture of 9.5 g. 3-sec.butylsulphonyl-1,2,4-triazole, 8.2 g. dipropylcarbamoyl chloride, 50 ml. dry tetrahydrofuran and 7.5 ml. dry triethylamine was refluxed under anhydrous conditions for 2 hours. The reaction mixture was worked up as described in Example 1 to produce a solid product which was recrystallized from a mixture of toluene and petroleum ether (b.p. 60° – 80° C.) to give 1-dipropylcarbamoyl-3-sec.-butylsulphonyl-1,2,4-triazole, m.p. 80° – 81° C. Elemental analysis satisfactory.

EXAMPLE 28

A mixture of 6.45 g. 3-ethylthio-1,2,4-triazole, 7.5 g. diethylcarbamoyl chloride, 40 ml. dry tetrahydrofuran and 7.75 ml. dry triethylamine was refluxed under anhydrous conditions for 22 hours. The reaction mixture was worked up as described in Example 1, using ether in place of methylene dichloride, to give a residual oil. This oil was distilled under reduced pressure to give 1-diethylcarbamoyl-3-ethylthio-1,2,4-triazole, b.p. 110° – 111° C./0.2 mm. (93.6% 1-isomer by GLC assay). Elemental analysis satisfactory.

EXAMPLE 29

A mixture of 4.8 g. 3-propylsulphinyl-1,2,4-triazole, 4.48 g. diethylcarbamoyl chloride, 40 ml. dry tetrahydrofuran and 6 ml. dry triethylamine was refluxed under anhydrous conditions for 5 hours. The cooled reaction mixture was filtered to remove triethylamine hydrochloride. The filtrate was diluted with petroleum ether (b.p. 40° – 60° C.), causing the deposition of an oil which gradually solidified. The solid product was collected and recrystallized from a mixture of ether and petroleum ether (b.p. 40° – 60° C.) to give 1-diethylcarbamoyl-3-propylsulphinyl-1,2,4-triazole, m.p. 50.5° – 51.5° C.

The following compounds were prepared in an analogous manner.

1-diethylcarbamoyl-3-n-butylsulphinyl-1,2,4-triazole, m.p. 64.5° – 65.5° C. (from ether/petroleum ether, b.p. 60° – 80° C.)

1-diethylcarbamoyl-3-methylsulphonyl-1,2,4-triazole, m.p. 89.5° – 90° C. (from benzene/petroleum ether, b.p. 40° – 60° C.)

1-diethylcarbamoyl-3-ethylsulphonyl-1,2,4-triazole, m.p. 53° – 53.5° C. (from benzene/petroleum ether, b.p. 40° – 60° C.)

1-diethylcarbamoyl-3-propylsulphonyl-1,2,4-triazole, m.p. 65° – 65.5° C. (from benzene/petroleum ether, b.p. 40° – 60° C.)

1-diethylcarbamoyl-3-n-butylsulphonyl-1,2,4-triazole, m.p. 60.5° – 61° C. (from benzene/petroleum ether, b.p. 40° – 60° C.)

1-diethylcarbamoyl-3-isopropylsulphonyl-1,2,4-triazole, m.p. 53.5° – 55.5° C. (from benzene/petroleum ether, b.p. 40° – 60° C.)

1-diethylcarbamoyl-3-isobutylsulphonyl-1,2,4-triazole, m.p. 53° – 54.5° C. (from benzene/petroleum ether, b.p. 40° – 60° C.)

1-diethylcarbamoyl-3-n-pentylsulphonyl-1,2,4-triazole, m.p. 37° – 39° C. (from toluene/petroleum ether, b.p. 40° – 60° C.)

1-(N-ethyl-N-isobutylcarbamoyl)-3-ethylsulphonyl-1,2,4-triazole, m.p. 70° – 70.5° C. (from ether/petroleum ether, b.p. 40° – 60° C.)

1-(N-propyl-N-isobutylcarbamoyl)-3-ethylsulphonyl-1,2,4-triazole, m.p. 61° – 61.5° C. (from benzene/petroleum ether, b.p. 40° – 60° C.)

1-(N-propyl-N-prop-2-ynylcarbamoyl)-3-ethylsulphonyl-1,2,4-triazole, m.p. 73° – 73.5° C. (from benzene/petroleum ether, b.p. 40° – 60° C.)

1-(N-n-butyl-N-ethylcarbamoyl)-3-ethylsulphonyl-1,2,4-triazole, m.p. 49° – 50° C. (from ether/petroleum ether, b.p. 40° – 60° C.)

Satisfactory elemental analyses were obtained for all the above compounds.

EXAMPLE 30

A mixture of 7.2 g. 3-propylthio-1,2,4-triazole, 6.8 g. diethylcarbamoyl chloride, 35 ml. dry tetrahydrofuran and 9 ml. dry triethylamine was refluxed under anhydrous conditions for 72 hours. The reaction mixture was worked up as described in Example 1 to produce a residual oil. This oil was distilled under reduced pressure to give 1-diethylcarbamoyl-3-propylthio-1,2,4-triazole, b.p. 118° – 121° C./0.2 mm. (89.9% 1-isomer by GLC assay). Elemental analysis satisfactory.

In a similar manner there was prepared the compound 1-diethylcarbamoyl-3-n-butylthio-1,2,4-triazole, b.p. 124° – 130° C./0.2 mm. (89.4% 1-isomer by GLC assay). Elemental analysis satisfactory.

EXAMPLE 31

A mixture of 6.45 g. 3-ethylthio-1,2,4-triazole, 8.1 g. N-propyl-N-prop-2-ynylcarbamoyl chloride, 25 ml. dry tetrahydrofuran and 8 ml. dry triethylamine was refluxed under anhydrous conditions for 24 hours. The reaction mixture was worked up as described in Example 1, using ether in place of methylene dichloride, to give a residual oil. This residual oil was distilled under reduced pressure to give 1-(N-propyl-N-prop-2-ynyl-carbamoyl)-3-ethylthio-1,2,4-triazole, b.p. 124° C./0.05 mm. (97.8% 1-isomer by GLC assay). Elemental analysis satisfactory.

The following compounds were prepared in an analogous manner.

1-(N-allyl-N-ethylcarbamoyl)-3-ethylthio-1,2,4-triazole, b.p. 120° – 122° C./0.05 mm. (95.5% 1-isomer by GLC assay).

1-(N-allyl-N-n-butylcarbamoyl)-3-ethylthio-1,2,4-triazole, b.p. 127° C./0.05 mm. (95.5% 1-isomer by GLC assay).

1-(N-allyl-N-propylcarbamoyl-3-ethylthio-1,2,4-triazole, b.p. 125° C./0.05 mm. (96.2% 1-isomer by GLC assay).

1-(N-allyl-N-n-hexylcarbamoyl)-3-ethylthio-1,2,4-triazole, b.p. 138° – 140° C./0.03 mm. (94.3% 1-isomer by GLC assay).

1-(N-allyl-N-n-pentylcarbamoyl)-3-ethylthio-1,2,4-triazole, b.p. 142° C./0.1 mm. (91.5% 1-isomer by GLC assay).

1-(N-n-butyl-N-ethylcarbamoyl)-3-ethylthio-1,2,4-triazole, b.p. 120° C./0.05 mm. (89.0% 1-isomer by GLC assay).

1-(N-ethyl-N-propylcarbamoyl)-3-ethylthio-1,2,4-triazole, b.p. 116° C./0.03 mm. (92.1% 1-isomer by GLC assay).

1-(N-ethyl-N-n-pentylcarbamoyl)-3-ethylthio-1,2,4-triazole, b.p. 125° C./0.05 mm. (86.4% 1-isomer by GLC assay).

1-(N-ethyl-N-n-hexylcarbamoyl)-3-ethylthio-1,2,4-triazole, b.p. 140° C./0.1 mm. (92.3% 1-isomer by GLC assay).

1-(N-allyl-N-isobutylcarbamoyl)-3-ethylthio-1,2,4-triazole, b.p. 127° – 130° C./0.2 mm. (94.9% 1-isomer by GLC assay).

1-(N-ethyl-N-isobutylcarbamoyl)-3-ethylthio-1,2,4-triazole, b.p. 120° – 121° C./0.2 mm. (90.1% 1-isomer by GLC assay).

1-(N-ethyl-N-isopentylcarbamoyl)-3-ethylthio-1,2,4-triazole, b.p. 133° C./0.5 mm. (89.3% 1-isomer by GLC assay).

1-(N-propyl-N-isobutylcarbamoyl)-3-ethylthio-1,2,4-triazole, b.p. 124° – 128° C./0.3 mm. (89.7% 1-isomer by GLC assay).

Satisfactory elemental analyses were obtained for all the above compounds.

EXAMPLE 32

A mixture of 5.16 g. 3-ethylthio-1,2,4-triazole, 7.8 g. N-n-butyl-N-propylcarbamoyl chloride, 35 ml. dry tetrahydrofuran and 8 ml. dry triethylamine was refluxed under anhydrous conditions for 24 hours. The reaction mixture was worked up as described in Example 1 to give a residual oil. This oil was distilled under reduced pressure to give 1-(N-n-butyl-N-propylcarbamoyl)-3-ethylthio-1,2,4-triazole, b.p. 127° C./0.2 mm. (91.2% 1-isomer by GLC assay). Elemental analysis satisfactory.

In an analogous manner, the following compound was prepared.

1-(N-n-pentyl-N-propylcarbamoyl)-3-ethylthio-1,2,4-triazole, b.p. 135° – 137° C./0.1 mm. (88.6% 1-isomer by GLC assay). Elemental analysis satisfactory.

EXAMPLE 33

A mixture of 4.83 g. 3-ethylsulphonyl-1,2,4-triazole, 6.0 g. N-n-pentyl-N-propylcarbamoyl chloride, 40 ml. dry tetrahydrofuran and 6 ml. dry triethylamine was refluxed under anhydrous conditions for 24 hours. The cooled reaction mixture was filtered. The filtrate was distilled under reduced pressure to give 1-(N-n-pentyl-N-propylcarbamoyl)-3-ethylsulphonyl-1,2,4-triazole as a residual oil, $n_D^{25}$ 1.4967. (96.5% 1-isomer by GLC assay). Elemental analysis satisfactory.

The following compound was prepared in an analogous maner.

1-(N-n-hexyl-N-propylcarbamoyl)-3-ethylsulphonyl-1,2,4-triazole, an oil, $n_D^{25}$ 1.4945. (95.5% 1-isomer by GLC assay). Elemental analysis satisfactory.

EXAMPLE 34

A mixture of 7.25 g. 3-ethylsulphinyl-1,2,4-triazole, 7.8 g. N-allyl-N-ethylcarbamoyl chloride, 7.5 ml. dry triethylamine and 100 ml. dry tetrahydrofuran was refluxed under anhydrous conditions for 4 hours. The cooled reaction mixture was filtered and the filtrate distilled under reduced pressure to give 1-(N-allyl-N-ethylcarbamoyl)-3-ethylsulphinyl-1,2,4-triazole as a residual oil, $n_D^{25}$ 1.5328.

The following compounds were prepared in an analogous manner.

1-(N-allyl-N-propylcarbamoyl)-3-ethylsulphinyl-1,2,4-triazole, m.p. 59° – 61° C. (from petroleum ether, b.p. 40° – 60° C./benzene)

1-(N-allyl-N-n-butylcarbamoyl)-3-ethylsulphinyl-1,2,4-triazole, m.p. 44° – 46° C. (from benzene/petroleum ether, b.p. 40° – 60° C.)

1-(N-allyl-N-n-pentylcarbamoyl)-3-ethylsulphinyl-1,2,4-triazole, m.p. 50° – 52° C. (from benzene/petroleum ether, b.p. 40° – 60° C.)

1-(N-allyl-N-n-hexylcarbamoyl)-3-ethylsulphinyl-1,2,4-triazole, m.p. 38° – 41° C. (from benzene/petroleum ether, b.p. 40° – 60° C.)

1-(N-n-butyl-N-ethylcarbamoyl)-3-ethylsulphinyl-1,2,4-triazole, an oil, $n_D^{25}$ 1.5160.

1-(N-ethyl-N-n-hexylcarbamoyl)-3-ethylsulphinyl-1,2,4-triazole, an oil, $n_D^{25}$ 1.5118.

1-(N-allyl-N-isobutylcarbamoyl)-3-ethylsulphinyl-1,2,4-triazole, an oil, $n_D^{25}$ 1.5230.

1-(N-ethyl-N-isobutylcarbamoyl)-3-ethylsulphinyl-1,2,4-triazole, an oil, $n_D^{26}$ 1.5167.

1-(N-ethyl-N-isopentylcarbamoyl)-3-ethylsulphinyl-1,2,4-triazole, an oil, $n_D^{25}$ 1.5127.

Satisfactory elemental analyses were obtained for all the above compounds.

EXAMPLE 35

A mixture of 6.45 g. 3-ethylsulphonyl-1,2,4-triazole, 5.9 g. N-allyl-N-ethylcarbamoyl chloride, 6.5 ml. dry triethylamine and 80 ml. dry tetrahydrofuran was refluxed under anhydrous conditions for 6 hours. The reaction mixture was worked up as described in Example 1 to produce a solid residue which was recrystallized from benzene/petroleum ether, b.p. 40° – 60° C. to give 1-(N-allyl-N-ethylcarbamoyl)-3-ethylsulphonyl-1,2,4-triazole, m.p. 41° – 43° C.

The following compounds were prepared in an analogous manner.

1-(N-allyl-N-propylcarbamoyl)-3-ethylsulphonyl-1,2,4-triazole, m.p. 39° – 41.5° C. (from benzene/petroleum ether, b.p. 40° – 60° C.)

1-(N-allyl-N-n-butylcarbamoyl)-3-ethylsulphonyl-1,2,4-triazole, an oil, $n_D^{25}$ 1.5094. (98.4% 1-isomer by GLC assay).

1-(N-allyl-N-n-pentylcarbamoyl)-3-ethylsulphonyl-1,2,4-triazole, an oil, $n_D^{25}$ 1.5057. (93.0% 1-isomer by GLC assay).

1-(N-allyl-N-n-hexylcarbamoyl)-3-ethylsulphonyl-1,2,4-triazole, an oil, $n_D^{26}$ 1.5034.

1-(N-ethyl-N-n-hexylcarbamoyl)-3-ethylsulphonyl-1,2,4-triazole, an oil, b.p. 183° – 185° C./0.2 mm. (95.4% 1-isomer by GLC assay).

1-(N-allyl-N-isobutylcarbamoyl)-3-ethylsulphonyl-1,2,4-triazole, an oil, $n_D^{25}$ 1.5096. (91.7% 1-isomer by GLC assay).

1-(N-ethyl-N-propylcarbamoyl)-3-ethylsulphonyl-1,2,4-triazole, an oil, $n_D^{26}$ 1.5057. (97.7% 1-isomer by GLC assay).

1-(N-ethyl-N-isopentylcarbamoyl)-3-ethylsulphonyl-1,2,4-triazole, an oil, $n_D^{26}$ 1.4984. (99.1% 1-isomer by GLC assay).

1-(N-propyl-N-sec.butylcarbamoyl)-3-ethylsulphonyl-1,2,4-triazole, an oil, $n_D^{23}$ 1.5008. (94.7% 1-isomer by GLC assay).

Satisfactory elemental analyses were obtained for all the above compounds.

EXAMPLE 36

3-Isobutylsulphonyl-1,2,4-triazole, m.p. 157° – 158.5° C., was prepared by the oxidation of 3-isobutylthio-1,2,4-triazole in a manner analogous to that described in Example 1.

A mixture of 9.5 g. 3-isobutylsulphonyl-1,2,4-triazole, 8.2 g. dipropylcarbamoyl chloride, 7.5 ml. dry triethylamine and 100 ml. dry tetrahydrofuran was refluxed under anhydrous conditions for 11 hours. The reaction mixture was worked up as described in Example 1, using ether in place of methylene dichloride, to give 1-dipropylcarbamoyl-3-isobutylsulphonyl-1,2,4-triazole, m.p. 62° – 63.5° C. (from petroleum ether, b.p. 62° – 68° C.).

The following compounds were prepared in an analogous manner.

1-diallylcarbamoyl-3-isobutylsulphonyl-1,2,4-triazole, an oil, $n_D^{25}$ 1.5137. (99.6% 1-isomer by GLC assay).

1-di(2-methylallyl)carbamoyl-3-ethylsulphonyl-1,2,4-triazole, m.p. 31° – 33° C.

1-di(2-methylallyl)carbamoyl-3-ethylthio-1,2,4-triazole, an oil, b.p. 132° – 134° C./0.2 mm. (94.5% 1-isomer by GLC assay).

Satisfactory elemental analyses were obtained for all the above compounds.

EXAMPLE 37

A mixture of 7.1 g. 3-allylthio-1,2,4-triazole, (m.p. 27° – 30° C., prepared from 3-mercapto-1,2,4-triazole in an analogous manner to that described in Example 1), 8.0 g. diallylcarbamoyl chloride, 7.5 ml. dry triethylamine and 100 ml. dry tetrahydrofuran was refluxed under anhydrous conditions for 48 hours. The reaction mixture was worked up as described in Example 1 to give 1-diallylcarbamoyl-3-allylthio-1,2,4-triazole, b.p. 120° – 122° C./0.1 mm. (95.2% 1-isomer by GLC assay).

The following compounds were prepared in an analogous manner.

1-(N-propyl-N-prop-2-ynylcarbamoyl)-3-allylthio-1,2,4-triazole, b.p. 122° – 124° C./0.1 mm. (94.6% 1-isomer by GLC assay).

1-dipropylcarbamoyl-3-allylthio-1,2,4-triazole, b.p. 133° – 135° C./2.0 mm. (85.5% 1-isomer by GLC assay).

Satisfactory elemental analyses were obtained for all the above compounds.

EXAMPLE 38

In a similar manner to that described in Example 29, there were prepared the following compounds.

1-diethylcarbamoyl-3-isopropylsulphinyl-1,2,4-triazole, m.p. 66° – 68° C. (from benzene/petroleum ether, b.p. 40° – 60° C.) Elemental analysis satisfactory.

1-diethylcarbamoyl-3-isobutylthio-1,2,4-triazole, m.p. 49.5° – 52° C. (from petroleum ether, b.p. 40° – 60° C.). Elemental analysis satisfactory.

EXAMPLE 39

In an analogous manner to that described in Example 30, there were prepared the following compounds.

1-diethylcarbamoyl-3-isopropylthio-1,2,4-triazole, b.p. 129° – 131° C./0.7 mm. (90.5% 1-isomer by GLC assay). Elemental analysis satisfactory.

1-diethylcarbamoyl-3-sec. butylthio-1,2,4-triazole, b.p. 136° – 138° C./0.7 mm. (89.7% 1-isomer by GLC assay). Elemental analysis satisfactory.

EXAMPLE 40

A solution of 25.8 g. 3-ethylthio-1,2,4-triazole and 15.8 g. dry pyridine in 100 ml. dry tetrahydrofuran was added dropwise to 200 ml. of a 10% w/v solution of phosgene in dry tetrahydrofuran (20 g. phosgene, 1 molecular proportion), with stirring and cooling to maintain the reaction temperature at 25° – 30° C. The mixture was stirred at 25° – 30° C. for a further period of 0.5 hour, and was then filtered to remove pyridine hydrochloride formed in the reaction. To the resulting solution of 3-ethylthio-1,2,4-triazole-1-carbonyl chloride was added dropwise a solution of 20.2 g. dipropylamine and 15.8 g. dry pyridine in 50 ml. dry tetrahydrofuran, with stirring and cooling to maintain the reaction temperature at 25° – 30° C. The mixture was stirred at 25° – 30° C. for a further period of 0.5 hour, and was then filtered to remove pyridine hydrochloride formed in the reaction. The filtrate was evaporated under reduced pressure to remove solvent and the residual oil was dissolved in methylene dichloride. The resulting solution was washed successively with 0.5N sodium hydroxide solution, water, and finally 0.5N hydrochloric acid. The washed solution was distilled under reduced pressure to give 1-dipropylcarbamoyl-3-ethylthio-1,2,4-triazole, b.p. 130° C./0.5 mm. Elemental analysis satisfactory.

EXAMPLE 41

A solution of 35.75 g. 3-propylthio-1,2,4-triazole in 150 ml. dry tetrahydrofuran was added dropwise to a stirred suspension of sodium hydride in mineral oil (14.4 g. of 50% suspension; 7.2 g. sodium hydride). The resulting mixture was refluxed with stirring for 1 hour.

Heating was discontinued, and 40.9 g. dipropylcarbamoyl chloride was added dropwise to the stirred mixture, causing the evolution of heat with consequent refluxing. The reaction mixture was refluxed with stirring overnight, cooled, and filtered to remove sodium chloride formed in the reaction. The filtrate was distilled under reduced pressure to remove solvent, and the residual oil was dissolved in methylene dichloride. The resulting solution was washed successively with 0.5N sodium hydroxide solution, water, and finally 0.5N hydrochloric acid. The washed solution was distilled under reduced pressure to give 1-dipropylcarbamoyl-3-propylthio-1,2,4-triazole, b.p. 128° - 120° C./0.1 mm. Elemental analysis satisfactory.

EXAMPLE 42

A solution of 51.6 g. 3-ethylthio-1,2,4-triazole and 31.6 g. dry pyridine in 100 ml. dry tetrahydrofuran was added dropwise to 200 ml. of a 10% w/v solution of phosgene in dry tetrahydrofuran (20 g. phosgene, 0.5 molecular proportion) with stirring and cooling to maintain the reaction temperature at 25° - 30° C. The mixture was stirred at 25° - 30° C. for a further period of 0.5 hour, and was then filtered to remove pyridine hydrochloride formed in the reaction. To the resulting solution 1,1'-carbonylbis(3-ethylthio-1,2,4-triazole) was added dropwise with stirring a solution of 20.2 g. dipropylamine in 50 ml. dry tetrahydrofuran. The mixture was stirred for a further period of 0.5 hour, and was then evaporated under reduced pressure to remove solvent. The residual oil was dissolved in methylene dichloride and the resulting solution was washed successively with 0.5N sodium hydroxide solution, water, and finally 0.5N hydrochloric acid. The washed solution was distilled under reduced pressure to give 1-dipropylcarbamoyl-3-ethylthio-1,2,4-triazole, b.p. 130° - 132° C./0.5 mm. Elemental analysis satisfactory.

EXAMPLE 43

A solution of 13.5 g. 1-dipropylcarbamoyl-3-propylthio-1,2,4-triazole and 100 vol. hydrogen peroxide solution (5.7 ml., 1.0 molecular proportion) in 450 ml. glacial acetic acid was kept at room temperature for 14 days. The resulting solution was evaporated to dryness under reduced pressure and the residual oil was dissolved in methylene dichloride. The resulting solution was washed successively with 0.5N sodium hydroxide solution, and 0.5N hydrochloric acid. Solvent was removed from the solution by distillation under reduced pressure to give a residual oil which solidified on cooling. The solid product was recrystallized from benzene/petroleum ether, b.p. 40° - 60° C. to give 1-dipropylcarbamoyl-3-propylsulphinyl-1,2,4-triazole, m.p. 51° - 52.5° C. Elemental analysis satisfactory.

EXAMPLE 44

To a solution of 13.5 g. 1-dipropylcarbamoyl-3-propylthio-1,2,4-triazole in 150 ml. glacial acetic acid was added a 58% w/w solution of peracetic acid in glacial acetic acid (16.5 ml., 2.5 molecular proportions). The resulting mixture was heated at 100° C. for 3 hours, and then the acetic acid was removed by distillation under reduced pressure. The residue was dissolved in methylene dichloride and the resulting solution worked up as described in Example 43 to give 1-dipropylcarbamoyl-3-propylsulphonyl-1,2,4-triazole, m.p. 79° - 80° C. (from benzene/petroleum ether, b.p. 40° - 60° C.) Elemental analysis satisfactory.

EXAMPLE 45

In an analogous manner to that described in Example 30, there was prepared 1-diethylcarbamoyl-3-n-pentylthio-1,2,4-triazole, b.p. 140° - 144° C./0.1 mm. (97.0% 1-isomer by GLC assay). Elemental analysis satisfactory.

EXAMPLE 46

In an analogous manner to that described in Example 37, the following compounds were prepared.
1-diallylcarbamoyl-3-(but-2-enylthio)-1,2,4-triazole, b.p. 143° - 145° C./0.3 mm. (94.6% 1-isomer by GLC assay). Elemental analysis satisfactory.
1-dipropylcarbamoyl-3-(but-2enylthio)-1,2,4-triazole, b.p. 128° - 130° C./0.1 mm. (85.8% 1-isomer by GLC assay). Elemental analysis satisfactory.

The intermediate 3-(but-2-enylthio)-1,2,4-triazole, m.p. 57° - 60° C., used in the above preparations was prepared from 3-mercapto-1,2,4-triazole in an analogous manner to that described in Example 1.

EXAMPLE 47

In an analogous manner to that described in Example 1, the following compounds of formula I were prepared.
1-(N-ethyl-N-butylcarbamoyl)-3-propylsulphonyl-1,2,4-triazole, m.p. 55° - 56° C.
1-(N-ethyl-N-butylcarbamoyl)-3-butylsulphonyl-1,2,4-triazole, m.p. 35° C.
1-(N-ethyl-N-propylcarbamoyl)-3-isobutylsulphonyl-1,2,4-triazole, m.p. 57° - 57.5° C.
1-(N-ethyl-N-propylcarbamoyl)-3-butylsulphonyl-1,2,4-triazole, m.p. 30° C.
1-(N-ethyl-N-propylcarbamoyl)-3-isopropylsulphonyl-1,2,4-triazole, m.p. 44° - 44.5° C.
1-(N-ethyl-N-propylcarbamoyl)-3-propylsulphonyl-1,2,4-triazole, m.p. 47.5° - 48° C.
1-(N-allyl-N-propylcarbamoyl)-3-isobutylsulphonyl-1,2,4-triazole, an oil, $n_D^{22}$ 1.5108 (99.9% 1-isomer by GLC assay)
1-(N-allyl-N-propylcarbamoyl)-3-butylsulphonyl-1,2,4-triazole, an oil, $n_D^{22}$ 1.5070
1-(N-allyl-N-propylcarbamoyl)-3-propylsulphonyl-1,2,4-triazole, m.p. 39° - 40° C.
1-(N-allyl-N-propylcarbamoyl)-3-isopropylsulphonyl-1,2,4-triazole, an oil, $n_D^{22}$ 1.5108 (97.9% 1-isomer by GLC assay)
1-diethylcarbamoyl-3-sec.butylsulphonyl-1,2,4-triazole, an oil, $n_D^{26}$ 1.5045 (98.1% 1-isomer by GLC assay)
1-(N-ethyl-N-isopropylcarbamoyl)-3-butylsulphonyl-1,2,4-triazole, an oil, $n_D^{22}$ 1.5010 (95.6% 1-isomer by GLC assay)
1-(N-allyl-N-isopropylcarbamoyl)-3-isobutylsulphonyl-1,2,4-triazole, an oil, $n_D^{22}$ 1.5065 (98.9% 1-isomer by GLC assay)
1-(N-ethyl-N-isopropylcarbamoyl)-3-isobutylsulphonyl-1,2,4-triazole, m.p. 43° - 44° C.
1-(N-allyl-N-isopropylcarbamoyl)-3-butylsulphonyl-1,2,4-triazole, an oil, $n_D^{22}$ 1.5072 (97.9% 1-isomer by GLC assay)
1-(N-allyl-N-isopropylcarbamoyl)-3-propylsulphonyl-1,2,4-triazole, an oil $n_D^{22}$ 1.5109 (98.3% 1-isomer by GLC assay)
1-(N-allyl-N-isopropylcarbamoyl)-3-isopropylsulphonyl-1,2,4-triazole, m.p. 51.5° - 52° C.

1-(N-ethyl-N-isopropylcarbamoyl)-3-isopropylsulphonyl-1,2,4-triazole, an oil, $n_D^{22}$ 1.5047 (96.1% 1-isomer by GLC assay)

1-(N-ethyl-N-isopropylcarbamoyl)-3-propylsulphonyl-1,2,4-triazole, an oil, $n_D^{22}$ 1.5038 (93.8% 1-isomer by GLC assay)

1-(N-ethyl-N-isopropylcarbamoyl)-3-ethylsulphonyl-1,2,4-triazole, an oil, $n_D^{22}$ 1.5078 (93.5% 1-isomer by GLC assay)

1-(N-allyl-N-ethylcarbamoyl)-3-isopropylsulphonyl-1,2,4-triazole, an oil, $n_D^{26}$ 1.5128 (99.4% 1-isomer by GLC assay)

1-(N-allyl-N-ethylcarbamoyl)-3-butylsulphonyl-1,2,4-triazole, m.p. 50° – 52° C.

1-(N-ethyl-N-hexylcarbamoyl)-3-propylsulphonyl-1,2,4-triazole, m.p. 69° – 71° C.

1-(N-ethyl-N-hexylcarbamoyl)-3-isopropylsulphonyl-1,2,4-triazole, an oil, $n_D^{26}$ 1.4934 (96.0% 1-isomer by GLC assay)

1-(N-allyl-N-ethylcarbamoyl)-3-propylsulphonyl-1,2,4-triazole, m.p. 46° – 48° C.

1-(N-ethyl-N-hexylcarbamoyl)-3-butylsulphonyl-1,2,4-triazole, m.p. 58° – 60° C.

1-(N-allyl-N-isopropylcarbamoyl)-3-ethylsulphonyl-1,2,4-triazole, an oil, $n_D^{22}$ 1.5147 (96.7% 1-isomer by GLC assay)

1-(N-propyl-N-prop-2-ynylcarbamoyl)-3-isopropylsulphonyl-1,2,4-triazole, m.p. 68.5° – 69° C.

1-(N-propyl-N-prop-2-ynylcarbamoyl)-3-butylsulphonyl-1,2,4-triazole, an oil, $n_D^{25}$ 1.5143 (97.0% 1-isomer by GLC assay)

1-(N-propyl-N-prop-2-ynylcarbamoyl)-3-isobutylsulphonyl-1,2,4-triazole, an oil, $n_D^{22}$ 1.5108 (98.3% 1-isomer by GLC assay)

1-(N-propyl-N-prop-2-ynylcarbamoyl)-3-propylsulphonyl-1,2,4-triazole, m.p. 49° – 50° C.

1-(N-propyl-N-1-methylbutylcarbamoyl)-3-propylsulphonyl-1,2,4-triazole, m.p. 55° – 58° C.

1-(N-ethyl-N-hexylcarbamoyl)-3-isobutylsulphonyl-1,2,4-triazole, m.p. 55° – 57° C.

1-(N-ethyl-N-isopentylcarbamoyl)-3-isobutylsulphonyl-1,2,4-triazole, an oil, $n_D^{22}$ 1.4928

1-(N-ethyl-N-isopentylcarbamoyl)-3-butylsulphonyl-1,2,4-triazole, an oil, $n_D^{22}$ 1.4955

1-(N-ethyl-N-isopentylcarbamoyl)-3-propylsulphonyl-1,2,4-triazole, an oil, $n_D^{22}$ 1.4989

1-(N-propyl-N-pentylcarbamoyl)-3-isobutylsulphonyl-1,2,4-triazole, m.p. 45° – 46° C.

1-(N-propyl-N-pentylcarbamoyl)-3-butylsulphonyl-1,2,4-triazole, m.p. 65° – 66° C., 1-(N-propyl-N-pentylcarbamoyl)-3-propylsulphonyl-1,2,4-triazole, an oil, $n_D^{22}$ 1.4946

1-(N-propyl-N-sec.butylcarbamoyl)-3-butylsulphonyl-1,2,4-triazole, an oil, $n_D^{22}$ 1.4975

1-(N-propyl-N-sec.butylcarbamoyl)-3-propylsulphonyl-1,2,4-triazole, an oil, $n_D^{22}$ 1.5005

1-(N-allyl-N-butylcarbamoyl)-3-butylsulphonyl-1,2,4-triazole, an oil, $n_D^{22}$ 1.5048

1-(N-allyl-N-butylcarbamoyl)-3-propylsulphonyl-1,2,4-triazole, an oil, $n_D^{22}$ 1.5063

1-(N-propyl-N-isopropylcarbamoyl)-3-butylsulphonyl-1,2,4-triazole, an oil, $n_D^{22}$ 1.4998

1-(N-propyl-N-isopropylcarbamoyl)-3-propylsulphonyl-1,2,4-triazole, an oil, $n_D^{22}$ 1.5012

1-(N-ethyl-N-isobutylcarbamoyl)-3-butylsulphonyl-1,2,4-triazole, an oil, $n_D^{22}$ 1.4996

1-(N-ethyl-N-isobutylcarbamoyl)-3-propylsulphonyl-1,2,4-triazole, m.p. 40° – 42° C.

1-(N-allyl-N-isobutylcarbamoyl)-3-propylsulphonyl-1,2,4-triazole, an oil, $n_D^{22}$ 1.5047

1-(N-propyl-N-1-methylbutylcarbamoyl)-3-isopropylsulphonyl-1,2,4-triazole, an oil, $n_D^{26}$ 1.4952 (90.6% 1-isomer by GLC assay)

1-(N-propyl-N-1-methylbutylcarbamoyl)-3-butylsulphonyl-1,2,4-triazole, an oil, $n_D^{26}$ 1.4926 (93.1% 1-isomer by GLC assay)

1-(N-allyl-N-prop-2-ynylcarbamoyl)-3-ethylsulphonyl-1,2,4-triazole, m.p. 63° – 64° C.

1-(N-allyl-N-prop-2-ynylcarbamoyl)-3-propylsulphonyl-1,2,4-triazole, an oil, $n_D^{22}$ 1.5250 (95.7% 1-isomer by GLC assay)

1-(N-allyl-N-prop-2-ynylcarbamoyl)-3-isopropylsulphonyl-1,2,4-triazole, m.p. 64° – 64.5° C.

1-(N-allyl-N-prop-2-ynylcarbamoyl)-3-butylsulphonyl-1,2,4-triazole, m.p. 46° – 46.5° C.

1-(N-allyl-N-prop-2-ynylcarbamoyl)-3-isobutylsulphonyl-1,2,4-triazole, an oil, $n_D^{22}$ 1.5208 (96.9% 1-isomer by GLC assay)

1-(N-propyl-N-pentylcarbamoyl)-3-isobutylsulphonyl-1,2,4-triazole, an oil, $n_D^{26}$ 1.4878 (86.8% 1-isomer by GLC assay)

1-(N-propyl-N-pentylcarbamoyl)-3-butylsulphonyl-1,2,4-triazole, m.p. 64° – 66° C.

1-(N-propyl-N-pentylcarbamoyl)-3-isopropylsulphonyl-1,2,4-triazole, an oil, $n_D^{26}$ 1.4914 (96.7% 1-isomer by GLC assay)

1-(N-propyl-N-pentylcarbamoyl)-3-propylsulphonyl-1,2,4-triazole, an oil, $n_D^{26}$ 1.4906 (93.7% 1-isomer by GLC assay)

1-(N-propyl-N-butylcarbamoyl)-3-isobutylsulphonyl-1,2,4-triazole, m.p. 43° – 45° C.

1-(N-propyl-N-butylcarbamoyl)-3-butylsulphonyl-1,2,4-triazole, an oil, $n_D^{26}$ 1.4922 (98.7% 1-isomer by GLC assay)

1-(N-propyl-N-butylcarbamoyl)-3-isopropylsulphonyl-1,2,4-triazole, an oil, $n_D^{26}$ 1.4958 (99.2% 1-isomer by GLC assay)

1-(N-propyl-N-butylcarbamoyl)-3-propylsulphonyl-1,2,4-triazole, m.p. 58° – 60° C.

1-(N-propyl-N-1-methylbutylcarbamoyl)-3-isobutylsulphonyl-1,2,4-triazole, an oil, $n_D^{26}$ 1.4916 (88.2% 1-isomer by GLC assay)

1-(N-allyl-N-pentylcarbamoyl)-3-propylsulphonyl-1,2,4-triazole, an oil, $n_D^{26}$ 1.5006 (97.7% 1-isomer by GLC assay)

1-(N-allyl-N-pentylcarbamoyl)-3-isopropylsulphonyl-1,2,4-triazole, an oil, $n_D^{26}$ 1.5022 (98.0% 1-isomer by GLC assay)

1-(N-allyl-N-pentylcarbamoyl)-3-butylsulphonyl-1,2,4-triazole, an oil, $n_D^{26}$ 1.4992 (98.4% 1-isomer by GLC assay)

1-(N-allyl-N-pentylcarbamoyl)-3-isobutylsulphonyl-1,2,4-triazole, an oil, $n_D^{26}$ 1.4984 (97.4% 1-isomer by GLC assay)

1-(N-ethyl-N-pentylcarbamoyl)-3-isobutylsulphonyl-1,2,4-triazole, m.p. 65° – 67° C.

1-(N-ethyl-N-pentylcarbamoyl)-3-butylsulphonyl-1,2,4-triazole, m.p. 51° – 54° C.

1-(N-ethyl-N-pentylcarbamoyl)-3-isopropylsulphonyl 1,2,4-triazole, an oil, $n_D^{26}$ 1.4986

1-(N-ethyl-N-pentylcarbamoyl)-3-propylsulphonyl-1,2,4-triazole, m.p. 48.5° – 50.5° C.

1-(N-allyl-N-hexylcarbamoyl)-3-isobutylsulphonyl-1,2,4-triazole, an oil, $n_D^{26}$ 1.4964 (96.7% 1-isomer by GLC assay)

1-(N-allyl-N-hexylcarbamoyl)-3-butylsulphonyl-1,2,4-triazole, an oil, $n_D^{26}$ 1.4976 (98.4% 1-isomer by GLC assay)

1-(N-allyl-N-hexylcarbamoyl)-3-isopropylsulphonyl-1,2,4-triazole, an oil, $n_D^{26}$ 1.5004 (98.5% 1-isomer by GLC assay)

1-(N-allyl-N-hexylcarbamoyl)-3-propylsulphonyl-1,2,4-triazole, an oil, $n_D^{26}$ 1.4984 (97.3% 1-isomer by GLC assay)

1-(N-ethyl-N-cyclohexylcarbamoyl)-3-butylsulphonyl-1,2,4-triazole, m.p. 57° – 60° C.

1-(N-ethyl-N-cyclohexylcarbamoyl)-3-propylsulphonyl-1,2,4-triazole, m.p. 56° – 59° C.

1-(N-ethyl-N-cyclohexylcarbamoyl)-3-ethylsulphonyl-1,2,4-triazole, an oil, $n_D^{26}$ 1.5208 (88.0% 1-isomer by GLC assay)

1-(N-ethyl-N-allylcarbamoyl)-3-sec.butylsulphonyl-1,2,4-triazole, m.p. 32° – 33° C.

1-(N-propyl-N-prop-2-ynylcarbamoyl)-3-sec.butylsulphonyl-1,2,4-triazole, m.p. 59° – 60° C.

1-(N-hexyl-N-allylcarbamoyl)-3-sec.butylsulphonyl-1,2,4-triazole, m.p. 45° – 46° C.

1-(N-butyl-N-propylcarbamoyl)-3-sec.butylsulphonyl-1,2,4-triazole, m.p. 50° – 51° C.

1-di-isopropylcarbamoyl-3-sec.butylsulphonyl-1,2,4-triazole, m.p. 85° – 87° C.

1-(N-ethyl-N-butylcarbamoyl)-3-sec.butylsulphonyl-1,2,4-triazole, an oil, $n_D^{20}$ 1.4995

1-(N-allyl-N-propylcarbamoyl)-3-sec.butylsulphonyl-1,2,4-triazole, m.p. 47° – 48° C.

1-diethylcarbamoyl-3-t.butylsulphonyl-1,2,4-triazole, m.p. 117° – 118° C.

1-diallylcarbamoyl-3-t.butylsulphonyl-1,2,4-triazole, m.p. 79° – 80° C.

1-(N-allyl-N-propylcarbamoyl)-3-t.butylsulphonyl-1,2,4-triazole, m.p. 78° – 79° C.

1-(N-ethyl-N-butylcarbamoyl)-3-t.butylsulphonyl-1,2,4-triazole, m.p. 71° – 72° C.

1-(N-allyl-N-ethylcarbamoyl)-3-t.butylsulphonyl-1,2,4-triazole, m.p. 79° – 80° C.

1-(N-ethyl-N-prop-2-ynylcarbamoyl)-3-propylsulphonyl-1,2,4-triazole, m.p. 70° – 73° C.

1-(N-ethyl-N-prop-2-ynylcarbamoyl)-3-butylsulphonyl-1,2,4-triazole, m.p. 70° – 72° C.

1-(N-ethyl-N-prop-2-ynylcarbamoyl)-3-isobutylsulphonyl-1,2,4-triazole, m.p. 87° – 88° C.

1-(N-ethyl-N-prop-2-ynylcarbamoyl)-3-ethylsulphonyl-1,2,4-triazole, m.p. 57° – 58° C.

1-(N-ethyl-N-isopropylcarbamoyl)-3-pentylsulphonyl-1,2,4-triazole, an oil, $n_D^{21}$ 1.5014 (95.8% 1-isomer by GLC assay)

1-(N-ethyl-N-isopropylcarbamoyl)-3-sec.butylsulphonyl-1,2,4-triazole, an oil, $n_D^{21}$ 1.5045 (96.1% 1-isomer by GLC assay)

1-(N-propyl-N-isopropylcarbamoyl)-3-isobutylsulphonyl-1,2,4-triazole, an oil, $n_D^{21}$ 1.5032 (95.2% 1-isomer by GLC assay)

1-(N-propyl-N-isopropylcarbamoyl)-3-isobutylsulphonyl-1,2,4-triazole, m.p. 61° – 63° C.

1-(N-propyl-N-isopropylcarbamoyl)-3-sec.butylsulphonyl-1,2,4-triazole, m.p. 68° – 70° C.

1-(N-propyl-N-isopropylcarbamoyl)-3-pentylsulphonyl-1,2,4-triazole, m.p. 54.5° – 56.5° C.

1-(N-propyl-N-prop-2-ynylcarbamoyl)-3-pentylsulphonyl-1,2,4-triazole, an oil, $n_D^{25}$ 1.5102 (93.4% 1-isomer by GLC assay)

1-(N-ethyl-N-prop-2-ynylcarbamoyl)-3-sec.butylsulphonyl-1,2,4-triazole, m.p. 62° – 65° C.

1-(N-propyl-N-sec.butylcarbamoyl)-3-isobutylsulphonyl-1,2,4-triazole, m.p. 35° – 38° C.

1-(N-propyl-N-sec.butylcarbamoyl)-3-pentylsulphonyl-1,2,4-triazole, m.p. 38° – 40° C.

1-(N-ethyl-N-prop-2-ynylcarbamoyl)-3-pentylsulphonyl-1,2,4-triazole, m.p. 47° – 50° C.

1-(N-ethyl-N-prop-2-ynylcarbamoyl)-3-isopropylsulphonyl-1,2,4-triazole, m.p. 90° – 91.5° C.

1-(N-propyl-N-sec.butylcarbamoyl)-3-isopropylsulphonyl-1,2,4-triazole, m.p. 39° – 41° C.

1-(N-propyl-N-sec.butylcarbamoyl)-3-sec.butylsulphonyl-1,2,4-triazole, m.p. 40° – 41° C.

1-(N-ethyl-N-allylcarbamoyl)-3-isobutylsulphonyl-1,2,4-triazole, m.p. 67° – 69° C.

1-(N-ethyl-N-sec.butylcarbamoyl)-3-isobutylsulphonyl-1,2,4-triazole, m.p. 39° – 40.5° C.

1-(N-ethyl-N-sec.butylcarbamoyl)-3-butylsulphonyl-1,2,4-triazole, m.p. 25° C.

1-(N-ethyl-N-butylcarbamoyl)-3-isopropylsulphonyl-1,2,4-triazole, an oil, $n_D^{26}$ 1.5010 (98.1% 1-isomer by GLC assay)

1-(N-ethyl-N-butylcarbamoyl)-3-isobutylsulphonyl-1,2,4-triazole, m.p. 58° – 60° C.

1-(N-ethyl-N-butylcarbamoyl)-3-pentylsulphonyl-1,2,4-triazole, an oil, $n_D^{26}$ 1.4970 (98.6% 1-isomer by GLC assay)

1-(N-allyl-N-ethylcarbamoyl)-3-pentylsulphonyl-1,2,4-triazole, an oil, $n_D^{26}$ 1.5080 (98.7% 1-isomer by GLC assay)

1-(N-allyl-N-hexylcarbamoyl)-3-pentylsulphonyl-1,2,4-triazole, an oil, $n_D^{26}$ 1.5003 (99.4% 1-isomer by GLC assay)

1-(N-allyl-N-propylcarbamoyl)-3-pentylsulphonyl-1,2,4-triazole, an oil, $n_D^{22}$ 1.5059 (99.6% 1-isomer by GLC assay)

1-(N-allyl-N-ethylcarbamoyl)-3-isobutylsulphonyl-1,2,4-triazole, m.p. 67° – 69° C.

1-(N-ethyl-N-isobutylcarbamoyl)-3-isobutylsulphonyl-1,2,4-triazole, m.p. about 25° C.

1-(N-ethyl-N-pentylcarbamoyl)-3-pentylsulphonyl-1,2,4-triazole, m.p. about 25° C.

1-(N-ethyl-N-pentylcarbamoyl)-3-ethylsulphonyl-1,2,4-triazole, m.p. about 25° C.

1-N-di(2-methylallyl)carbamoyl-3-isobutylsulphonyl-1,2,4-triazole, an oil, $n_D^{22}$ 1.5130 (99.5% 1-isomer by GLC assay)

1-N-di(2-methylallyl)carbamoyl-3-pentylsulphonyl-1,2,4-triazole, an oil, $n_D^{22}$ 1.5113 (99.4% 1-isomer by GLC assay)

1-(N-butyl-N-allylcarbamoyl)-3-pentylsulphonyl-1,2,4-triazole, an oil, $n_D^{26}$ 1.5003 (95% 1-isomer by GLC assay)

1-N-allyl-N-butylcarbamoyl-3-sec.butylsulphonyl-1,2,4-triazole, an oil, $n_D^{26}$ 1.5040 (95% 1-isomer by GLC assay)

1-(N-allyl-N-butylcarbamoyl)-3-sec.butylsulphonyl-1,2,4-triazole, an oil, $n_D^{26}$ 1.5025 (95.7% 1-isomer by GLC assay)

1-(N-allyl-N-butylcarbamoyl)-3-isopropylsulphonyl-1,2,4-triazole, an oil, $n_D^{25}$ 1.5076 (95.1% 1-isomer by GLC assay)

1-(N-allyl-N-isopropylcarbamoyl)-3-pentylsulphonyl-1,2,4-triazole, an oil, $n_D^{26}$ 1.5058 (97.8% 1-isomer by GLC assay)

1-(N-allyl-N-isopropylcarbamoyl)-3-sec.butylsulphonyl-1,2,4-triazole, an oil, $n_D^{26}$ 1.5076 (96.9% 1-isomer by GLC assay)

1-N-di(2-methylallyl)carbamoyl-3-butylsulphonyl-1,2,4-triazole, an oil, $n_D^{22}$ 1.5118 (99.3% 1-isomer by GLC assay)

1-N-di(2-methylallyl)carbamoyl-3-propylsulphonyl-1,2,4-triazole, an oil, $n_D^{22}$ 1.5152

1-N-di(2-methylallyl)carbamoyl-3-isopropylsulphonyl-1,2,4-triazole, an oil, $n_D^{22}$ 1.5163 (98.6% 1-isomer by GLC assay)

1-(N-ethyl-N-hexylcarbamoyl)-3-pentylsulphonyl-1,2,4-triazole, m.p. 56° – 57° C.

1-(N-ethyl-N-hexylcarbamoyl)-3-sec.butylsulphonyl-1,2,4-triazole, an oil, $n_D^{22}$ 1.4966 (95.8% 1-isomer by GLC assay)

1-(N-allyl-N-isobutylcarbamoyl)-3-isopropylsulphonyl-1,2,4-triazole, an oil, $n_D^{26}$ 1.5075 (99.6% 1-isomer by GLC assay)

1-(N-allyl-N-isobutylcarbamoyl)-3-butylsulphonyl-1,2,4-triazole, an oil, $n_D^{26}$ 1.5046 (99.2% 1-isomer by GLC assay)

1-(N-allyl-N-isobutylcarbamoyl)-3-isobutylsulphonyl-1,2,4-triazole, an oil $n_D^{26}$ 1.5036 (98.1% 1-isomer by GLC assay)

1-(N-allyl-N-isobutylcarbamoyl)-3-sec.butylsulphonyl-1,2,4-triazole, an oil, $n_D^{26}$ 1.5050 (98.3% 1-isomer by GLC assay)

1-(N-allyl-N-isobutylcarbamoyl)-3-pentylsulphonyl-1,2,4-triazole, an oil, $n_D^{26}$ 1.5002 (99.2% 1-isomer by GLC assay)

1-(N-allyl-N-pentylcarbamoyl)-3-pentylsulphonyl-1,2,4-triazole, an oil, $n_D^{22}$ 1.5006 (97.6% 1-isomer by GLC assay)

1-(N-allyl-N-pentylcarbamoyl)-3-sec.butylsulphonyl-1,2,4-triazole, an oil, $n_D^{22}$ 1.5042 (96.4% 1-isomer by GLC assay)

EXAMPLE 48

In an analogous manner to that described in Example 2, the following compounds of formula I were prepared.

1-(N-allyl-N-prop-2-ynylcarbamoyl)-3-ethylthio-1,2,4-triazole, b.p. 127° – 131° C./0.2 mm. (97.2% 1-isomer by GLC assay)

1-(N-allyl-N-isopropylcarbamoyl)-3-ethylthio-1,2,4-triazole, b.p. 117° – 119° C./0.2mm. (81.7% 1-isomer by GLC assay)

1-(N-ethyl-N-isopropylcarbamoyl)-3-ethylthio-1,2,4-triazole, b.p. 112° – 115° C./0.15 – 0.2 mm. (72.7% 1-isomer by GLC assay)

1-(N-allyl-N-prop-2-ynylcarbamoyl)-3-ethylthio-1,2,4-triazole, b.p. 125° – 127° C./0.11 mm. (96.0% 1-isomer by GLC assay)

1-diethylcarbamoyl-3-t.butylthio-1,2,4-triazole, b.p. 141° – 142° C./1.4 mm.

1-diallylcarbamoyl-3-t.butylthio-1,2,4-triazole, b.p. 124° C./0.2 mm. (97.4% 1-isomer by GLC assay)

1-(N-allyl-N-propylcarbamoyl)-3-t.butylthio-1,2,4-triazole, b.p. 150° – 151° C./1.3 mm.

1-(N-ethyl-N-butylcarbamoyl)-3-t.butylthio-1,2,4-triazole, b.p. 161° – 162° C./2.7 mm. (93.4% 1-isomer by GLC assay)

EXAMPLE 49

A dispersible powder was prepared by grinding together a mixture of the following ingredients in a hammer mill.

|  | % w/w |
|---|---|
| 1-Dipropylcarbamoyl-3-propylsulphonyl-1,2,4-triazole | 25.0 |
| Sodium N-methyl-N-palmitoyltaurate | 6.0 |
| Sodium di-octylsulphosuccinate | 0.5 |
| Colloidal silicic acid | 25.0 |
| Kaolin | 43.5 |

Similar dispersible powders were prepared using the following active ingredients in place of the triazole compound in the above formulation.

1-dipropylcarbamoyl-3-n-butylsulphonyl-1,2,4-triazole 1-dipropylcarbamoyl-3-ethylsulphonyl-1,2,4-triazole 1-dipropylcarbamoyl-3-isopropylsulphonyl-1,2,4-triazole 1-dipropylcarbamoyl-3-sec.butylsulphonyl-1,2,4-triazole 1-diallylcarbamoyl-3-propylsulphonyl-1,2,4-triazole 1-diethylcarbamoyl-3-methylsulphonyl-1,2,4-triazole 1-diethylcarbamoyl-3-n-butylsulphinyl-1,2,4-triazole 1-(N-n-butyl-N-ethylcarbamoyl)-3-ethylsulphonyl-1,2,4-triazole 1-(N-propyl-N-prop-2-ynylcarbamoyl)-3-ethylsulphonyl-1,2,4-triazole 1-(N-ethyl-N-isobutylcarbamoyl)-3-ethylsulphonyl-1,2,4-triazole

EXAMPLE 50

An emulsifiable concentrate suitable for dilution with water to form an aqueous emulsion was prepared from the following ingredients.

|  | % w/w |
|---|---|
| 1-Diallylcarbamoyl-3-ethylthio-1,2,4-triazole | 20.0 |
| Calcium dodecylbenzenesulphonate | 2.5 |
| Nonylphenoxypolyethoxyethanol* | 2.5 |
| Xylene | to 100.0 |

*A nonylphenol-ethylene oxide condensate containing an average of 14 mols. ethylene oxide per mol. nonylphenol.

Similar emulsifiable concentrates were prepared in which the triazole compound in the above formulation was replaced by the following compounds.

1-dipropylcarbamoyl-3-n-butylsulphonyl-1,2,4,-triazole 1-dipropylcarbamoyl-3-ethylsulphonyl-1,2,4-triazole 1-dipropylcarbamoyl-3-n-pentylsulphinyl-1,2,4-triazole 1-diallylcarbamoyl-3-propylsulphinyl-1,2,4-triazole 1-diallylcarbamoyl-3-ethylsulphonyl-1,2,4-triazole 1-diethylcarbamoyl-3-ethylthio-1,2,4-triazole 1-diallylcarbamoyl-3-n-butylsulphonyl-1,2,4-triazole 1-(N-allyl-N-isobutylcarbamoyl)-3-ethylsulphonyl-1,2,4-triazole 1-(N-allyl-N-isobutylcarbamoyl)-3-ethylsulphinyl-1,2,4-triazole 1-(N-propyl-N-sec.butylcarbamoyl)-3-ethylsulphonyl-1,2,4-triazole

EXAMPLE 51

Emulsifiable concentrates (A) and (B) were prepared as described in Example 48, containing the following compounds as active ingredients:

(A) 1-diallylcarbamoyl-3-ethylthio-1,2,4-triazole (B) 1-dipropylcarbamoyl-3-ethylsulphonyl-1,2,4-triazole Rice seedlings were transplanted into paddy plots previously seeded with barnyard grass. Five days later the plots were sprayed with aqueous emulsions prepared from the concentrates (A) and (B), at an application rate of active ingredient of 2lb./acre. The plots were flooded with water six days later and examined 35 days after spraying. No barnyard grass was observed in the plots sprayed with the aqueous emulsions described above, and no phytotoxic effect on the rice plants was observed. A growth of barnyard grass had occurred in control plots that had received no chemical treatment.

We claim:

1. A herbicidal composition which comprises a carrier and a herbicidally effective amount of a compound of the formula

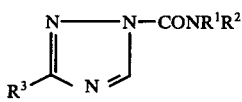

in which $R^3$ is selected from the group consisting of alkylthio containing 2–5 carbon atoms, alkylsulphinyl containing 3–5 carbon atoms, alkylsulphonyl containing 1–5 carbons atoms and alkenylthio containing 3–4 carbon atoms, $R^1$ is selected from the group consisting of alkyl containing 2–6 carbon atoms, allyl and 2-methylallyl and $R^2$, which together with $R^1$ contains a total of 4–9 carbon atoms, is selected from the group consisting of alkyl containing 2–3 carbon atoms, allyl, 2-methylallyl and prop-2-ynyl.

2. A herbicidal composition according to claim 1 comprising a compound in which $R^3$ is alkylsulphonyl containing 1–5 carbon atoms and the carbamoyl group $CONR^1R^2$ contains 5–10 carbon atoms and is selected from the group consisting of diallylcarbamoyl, dialkylcarbamoyl, N-allyl-N-alkylcarbamoyl and N-alkyl-N-prop-2-ynylcarbamoyl.

3. A herbicidal composition according to claim 2 comprising a compound in which $R^3$ contains 1–4 carbon atoms and the carbamoyl group is dialkylcarbamoyl wherein the alkyl reaicals are the same or different.

4. A herbicidal composition according to claim 2 comprising a compound in which $R^3$ contains 1–4 carbon atoms and the carbamoyl group is selected from the group consisting of dipropylcarbamoyl, N-propyl-N-isopropylcarbamoyl, di-isopropylcarbamoyl and N-ethyl-N-propylcarbamoyl.

5. A herbicidal composition according to claim 1 comprising a compound in which $R^3$ is alkylsulphinyl containing 3–5 carbon atoms and the carbamoyl group $CONR^1R^2$ contains 5–10 carbon atoms and is selected from the group consisting of diallylcarbamoyl, dialkylcarbamoyl, N-allyl-N-alkylcarbamoyl and N-alkyl-N-prop-2-ynylcarbamoyl.

6. A herbicidal composition according to claim 1 comprising a compound in which $R^3$ is alkylthio containing 2–5 carbon atoms and the carbamoyl group $CONR^1R^2$ contains 5–10 carbon atoms and is selected from the group consisting of diallylcarbamoyl, N-allyl-N-alkylcarbamoyl and N-alkyl-N-prop-2-ynylcarbamoyl.

7. A herbicidal composition according to claim 6 comprising a compound in which $R^3$ contains 2–4 carbon atoms and the carbamoyl group is diallylcarbamoyl.

8. A herbicidal composition according to claim 1 which comprises a herbicidally effective amount of 1-(N-ethyl-N-propylcarbamoyl)-3-propylsulphonyl-1,2,4-triazole.

9. A method for the pre-weed emergence control of graminaceous weeds which comprises applying to the locus of the weeds a herbicidally effective amount of a compound of the formula

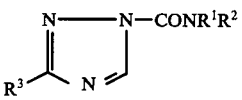

in which $R^3$ is selected from the group consisting of alkylthio containing 2–5 carbon atoms, alkylsulphinyl containing 3–5 carbon atoms, alkylsulphonyl containing 1–5 carbon atoms and alkenylthio containing 3–4 carbon atoms, $R^1$ is selected from the group consisting of alkyl containing 2–6 carbon atoms, allyl and 2-methylallyl and $R^2$, which together with $R^1$ contains a total of 4–9 carbon atoms, is selected from the group consisting of alkyl containing 2–3 carbon atoms, allyl, 2-methylallyl and prop-2-ynyl.

10. A method according to claim 9 in which graminaceous weeds are selectively controlled in a crop area by applying the compound to the crop area at an application rate sufficient to control the weeds but substantially nonphytotoxic to the crop.

11. A method according to claim 10 in which the crop area is selected from the group consisting of cotton, soyabean, maize and peanut.

* * * * *